(12) United States Patent
Huang et al.

(10) Patent No.: US 9,835,633 B1
(45) Date of Patent: Dec. 5, 2017

(54) COMPOSITIONS AND METHODS FOR IDENTIFYING AGENTS FOR TREATING APOE-RELATED DISEASES

(71) Applicant: The J. David Gladstone Institutes, San Francisco, CA (US)

(72) Inventors: Yadong Huang, San Francisco, CA (US); Qin Xu, Burlingame, CA (US)

(73) Assignee: The J. David Gladstone Institutes, San Francisco, CA (US)

(*) Notice: Subject to any disclaimer, the term of this patent is extended or adjusted under 35 U.S.C. 154(b) by 0 days.

(21) Appl. No.: 15/143,298

(22) Filed: Apr. 29, 2016

Related U.S. Application Data

(60) Provisional application No. 62/155,868, filed on May 1, 2015.

(51) Int. Cl.
| | |
|---|---|
| G01N 33/50 | (2006.01) |
| G01N 33/52 | (2006.01) |
| G01N 33/68 | (2006.01) |

(52) U.S. Cl.
CPC ..... *G01N 33/6896* (2013.01); *G01N 2333/47* (2013.01); *G01N 2333/95* (2013.01); *G01N 2500/10* (2013.01); *G01N 2500/20* (2013.01)

(58) Field of Classification Search
CPC ........... G01N 2500/10; G01N 2500/20; G01N 33/5008; G01N 33/5058; G01N 33/52; G01N 33/582; G01N 33/92; G01N 233/775; G01N 2333/811; G01N 2333/96411

See application file for complete search history.

(56) References Cited

U.S. PATENT DOCUMENTS

2012/0129782 A1* 5/2012 Huang ............... A61K 31/7088 514/17.8

FOREIGN PATENT DOCUMENTS

WO    WO 2010059942    5/2010

OTHER PUBLICATIONS

Choi S & Korstanje R. Proprotein convertases in high-density lipoprotein metabolism. Biomarker Research, 2013, 1:27 (8 pages).*
Tamboli Iy et al. Extracellular proteolysis of apolipoprotein E (apoE) by secreted serine neuronal protease. PLoS ONE, Mar. 2014, 9(3):e93120.*
Winsky-Sommerer R et al. The proprotein convertase PC2 is involved in the maturation of prosomatostatin to somatostatin-14 but not in the somatostatin deficit in Alzheimer's disease. Neuroscience, 2003, 122:437-447.*
Brecht WJ et al. Neuron-specific apolipoprotein E4 proteolysis is associated with increased tau phosphorylation in brains of transgenic mice. J. Neurosci. 2004, 24(10):2527-2534.*
Bartge et al; (1988) "Transgenic mice express the human phenylethanolamine N-methyltransferase gene in adrenal medulla and retina"; *Proc. Natl. Acad. Sci. USA* 85:3; pp. 648-3652.

Brecht et al; (2004) "Neuron-specific apolipoprotein e4 proteolysis is associated with increased tau phosphorylation in brains of transgenic mice"; *J. Neurosci.* 24; pp. 2527-2537.
Chen et al. (1987) "A lymphoproliferative abnormality associated with inappropriate expression of the Thy-1 antigen in transgenic mice"; *Cell* 51; pp. 7-19.
Choi and Korstanje (2013) "Proprotein convertases in high-density lipoprotein metabolism"; Biomark. Res. 1; pp. 27.
Comb et al; (1988) "Proteins bound at adjacent DNA elements act synergistically to regulate human proenkephalin cAMP inducible transcription"; *EMBO J.* 17; pp. 3793-3805.
EMBL HSENO2, X51956 "Human ENO2 gene for neuron specific (gamma) enolase"; GenBank: X51956.1, dated Oct. 23, 2008.
Frank et al; (2013) "Severe obesity and diabetes insipidus in a patient with PCSK1 deficiency"; *Mol. Genet. Metab.* 110; pp. 191-194.
GenBank NP_000032.1, "apolipoprotein E isoform b precursor [*Homo sapiens*]" dated Aug. 13, 2016.
GenBank HUMNFL, L04147, "Human neurofilament light chain (NEFL) gene, promoter region" dated Jan. 7, 1995.
GenBank HUMSYNIB, M55301, "Human synapsin I gene, 5' end", dated Jan. 13, 1995.
GenBank 562283.1, "5HT1C serotonin receptor {promoter region} [mice, Genomic, 1859 nt]", dated Aug. 25, 1993.
Harrington, et al; (1987) "Identification and cell type specificity of the tyrosine hydroxylase gene promoter"; *Nucl. Acids. Res.* 15(5); pp. 2363-2384.
Hokama, et al; (2013) "Altered Expression of Diabetes-Related Genes in Alzheimer's Disease Brains: TheHisayama Study"; *Cereb Cortex* 24(9):2476-88. doi: 10.1093/cercor/bht101. Epub Apr. 17, 2013.
Kaneda, et al; (1991)"Tissue-specific and high-level expression of the human tyrosine hydroxylase gene in transgenic mice"; *Neuron* 6(4); pp. 583-594.
Liu et al; (2004) "CMV enhancer/human PDGF—β promoter for neuron-specific transgene expression"; *Gene Therapy* 11; pp. 52-60.
Oberdick et al; (1990) "A promoter that drives transgene expression in cerebellar Purkinje and retinal bipolar neurons"; *Science* 248; pp. 223-226.
Ozawa et al; (2010) "Modulation of Prohormone Convertase 1/3 Properties Using Site-Directed Mutagenesis"; *Endocrinology*, 151(9); pp. 4437-4445.
Pickett et al; (2013) "Functional consequences of a novel variant of PCSK1"; *PLoSOne* 8(1); e55065.
Radovick et al; (1991) "Migratory arrest of gonadotropin-releasing hormone neurons in transgenic mice"; *Proc. Natl. Acad. Sci. USA* 88(8); pp. 3402-3406.
Rall et al; (1982) "Human apolipoprotein E. The complete amino acid sequence";J. Biol. Chem.257; pp. 4171-4178.
Weisgraber (1994) "Apolipoprotein E: structure-function relationships"; *Adv. Protein Chem.* 45; pp. 249-302.
Zhou and Mains (1994) "Endoproteolytic processing of proopiomelanocortin and prohormone convertases 1 and 2 in neuroendocrine cells overexpressing prohormone convertases 1 or 2"; *J. Biol. Chem.* 269; pp. 17440.

\* cited by examiner

*Primary Examiner* — Kimberly A. Ballard
(74) *Attorney, Agent, or Firm* — Michael B. Rubin; Bozicevic, Field & Francis LLP

(57) ABSTRACT

The present disclosure provides methods of identifying a candidate agent for treating an apoE-associated neurodegenerative disorder. The methods involve contacting a PCSK1 or a PCSK2 polypeptide with an apolipoprotein E polypeptide in the presence of a test agent.

13 Claims, 14 Drawing Sheets

Note: RFP is control transfection.

Note: C1-C6 indicate different shRNAs of PCSK1.

Note: A2, C5, C12, G1, and H11 indicate different shRNAs of PCSK2.

Note: A10, B1, B2, B4, and B5 indicate different shRNAs of 7B2.

Reduced ApoE Fragmentation in PCSK1/NSE-ApoE4 Mouse Brains (Day1 Pups)

Reduced ApoE Fragmentation and Increased Full Length ApoE in PCSK2/NSE-ApoE4 Mouse Hippocampus (6 Month)

Reduced ApoE Fragmentation and Increased Full Length ApoE in PCSK2/NSE-ApoE4 Mouse Cortex (6 Month)

FIGURE 7A
Human PCSK1 (Uniprot #:P29120)

Amino acid sequence
Isoform 1(canonical sequence, P29120-1 NCBI Reference Sequence: NM_000439.4)

MERRAWSLQCTAFVLFCAWCALNSAKAKRQFVNEWAAEIPGGPEAASAIAEELGYDLLGQ
IGSLENHYLFKHKNHPRRSRRSAFHITKRLSDDDRVIWAEQQYEKERSKRSALRDSALNL
FNDPMWNQQWYLQDTRMTAALPKLDLHVIPVWQKGITGKGVVITVLDDGLEWNHTDIYAN
YDPEASYDFNDNDHDPFPRYDPTNENKHGTRCAGEIAMQANNHKCGVGVAYNSKVGGIRM
LDGIVTDAIEASSIGFNPGHVDIYSASWGPNDDGKTVEGPGRLAQKAFEYGVKQGRQGKG
SIFVWASGNGGRQGDNCDCDGYTDSIYTISISSASQQGLSPWYAEKCSSTLATSYSSGDY
TDQRITSADLHNDCTETHTGTSASAPLAAGIFALALEANPNLTWRDMQHLVVWTSEYDPL
ANNPGWKKNGAGLMVNSRFGFGLLNAKALVDLADPRTWRSVPEKKECVVKDNDFEPRALK
ANGEVIIEIPTRACEGQENAIKSLEHVQFEATIEYSRRGDLHVTLTSAAGTSTVLLAERE
RDTSPNGFKNWDFMSVHTWGENPIGTWTLRITDMSGRIQNEGRIVNWKLILHGTSSQPEH
MKQPRVYTSYNTVQNDRRGVEKMVDPGEEQPTQENPKENTLVSKSPSSSSVGGRRDELEE
GAPSQAMLRLLQSAFSKNSPPKQSPKKSPSAKLNIPYENFYEALEKLNKPSQLKDSEDSL
YNDYVDVFYNTKPYKHRDDRLLQALVDILNEEN

FIGURE 7B
Isoform 2: (P29120-2; NCBI Reference Sequence: NM_001177875.1)
The sequence of this isoform differs from the canonical sequence as follows: 1-59:
MERRAWSLQCTAFVLFCAWCALNSAKAKRQFVNEWAAEIPGGPEAASAIAEELGYDLLG
→ MGKGSISFLFFS MGKGSISFLFFSQIGSLENHYLFKHKNHPRRSRRSAFHITKRLSDDDRVIWAEQQYEKER
SKRSALRDSALNLFNDPMWNQQWYLQDTRMTAALPKLDLHVIPVWQKGITGKGVVITVLD
DGLEWNHTDIYANYDPEASYDFNDNDHDPFPRYDPTNENKHGTRCAGEIAMQANNHKCGV
GVAYNSKVGGIRMLDGIVTDAIEASSIGFNPGHVDIYSASWGPNDDGKTVEGPGRLAQKA
FEYGVKQGRQGKGSIFVWASGNGGRQGDNCDCDGYTDSIYTISISSASQQGLSPWYAEKC
SSTLATSYSSGDYTDQRITSADLHNDCTETHTGTSASAPLAAGIFALALEANPNLTWRDM
QHLVVWTSEYDPLANNPGWKKNGAGLMVNSRFGFGLLNAKALVDLADPRTWRSVPEKKEC
VVKDNDFEPRALKANGEVIIEIPTRACEGQENAIKSLEHVQFEATIEYSRRGDLHVTLTS
AAGTSTVLLAERERDTSPNGFKNWDFMSVHTWGENPIGTWTLRITDMSGRIQNEGRIVNW
KLILHGTSSQPEHMKQPRVYTSYNTVQNDRRGVEKMVDPGEEQPTQENPKENTLVSKSPS
SSSVGGRRDELEEGAPSQAMLRLLQSAFSKNSPPKQSPKKSPSAKLNIPYENFYEALEKL
NKPSQLKDSEDSLYNDYVDVFYNTKPYKHRDDRLLQALVDILNEEN

FIGURE 8

Mouse PCSK1 (Uniprot #:P63239)

Amino acid sequence (P63239-1; NCBI Reference Sequence: NM_013628.2):

MEQRGWTLQCTAFAFFCVWCALNSVKAKRQFVNEWAAEIPGGQEAASAIAEELGYDLLGQ
IGSLENHYLFKHKSHPRRSRRSALHITKRLSDDDRVTWAEQQYEKERSKRSVQKDSALDL
FNDPMWNQQWYLQDTRMTAALPKLDLHVIPVWEKGITGKGVVITVLDDGLEWNHTDIYAN
YDPEASYDFNDNDHDPFPRYDLTNENKHGTRCAGEIAMQANNHKCGVGVAYNSKVGGIRM
LDGIVTDAIEASSIGFNPGHVDIYSASWGPNDDGKTVEGPGRLAQKAFEYGVKQGRQGKG
SIFVWASGNGGRQGDNCDCDGYTDSIYTISISSASQQGLSPWYAEKCSSTLATSYSSGDY
TDQRITSADLHNDCTETHTGTSASAPLAAGIFALALEANPNLTWRDMQHLVVWTSEYDPL
ASNPGWKKNGAGLMVNSRFGFGLLNAKALVDLADPRTWRNVPEKKECVVKDNNFEPRALK
ANGEVIVEIPTRACEGQENAIKSLEHVQFEATIEYSRRGDLHVTLTSAVGTSTVLLAERE
RDTSPNGFKNWDFMSVHTWGENPVGTWTLKITDMSGRMQNEGRIVNWKLILHGTSSQPEH
MKQPRVYTSYNTVQNDRRGVEKMVNVVEKRPTQKSLNGNLLVPKNSSSSNVEGRRDEQVQ
GTPSKAMLRLLQSAFSKNALSKQSPKKSPSAKLSIPYESFYEALEKLNKPSKLEGSEDSL
YSDYVDVFYNTKPYKHRDDRLLQALMDILNEEN

FIGURE 9A
Human PCSK2 (uniport #: P16519)

Isoform 1(canonical sequence, P16519-1; NCBI Reference Sequence: NM_002594.4)

MKGGCVSQWKAAAGFLFCVMVFASAERPVFTNHFLVELHKGGEDKARQVAAEHGFGVRKL
PFAEGLYHFYHNGLAKAKRRRSLHHKQQLERDPRVKMALQQEGFDRKKRGYRDINEIDIN
MNDPLFTKQWYLINTGQADGTPGLDLNVAEAWELGYTGKGVTIGIMDDGIDYLHPDLASN
YNAEASYDFSSNDPYPYPRYTDDWFNSHGTRCAGEVSAAANNNICGVGVAYNSKVAGIRM
LDQPFMTDIIEASSISHMPQLIDIYSASWGPTDNGKTVDGPRELTLQAMADGVNKGRGGK
GSIYVWASGDGGSYDDCNCDGYASSMWTISINSAINDGRTALYDESCSSTLASTFSNGRK
RNPEAGVATTDLYGNCTLRHSGTSAAAPEAAGVFALALEANLGLTWRDMQHLTVLTSKRN
QLHDEVHQWRRNGVGLEFNHLFGYGVLDAGAMVKMAKDWKTVPERFHCVGGSVQDPEKIP
STGKLVLTLTTDACEGKENFVRYLEHVQAVITVNATRRGDLNINMTSPMGTKSILLSRRP
RDDDSKVGFDKWPFMTTHTWGEDARGTWTLELGFVGSAPQKGVLKEWTLMLHGTQSAPYI
DQVVRDYQSKLAMSKKEELEEELDEAVERSLKSILNKN

FIGURE 9B
Isoform 2(P16519-2; NCBI Reference Sequence: NM_001201529.2)
The sequence of this isoform differs from the canonical sequence as follows:
    60-94: Missing.
MKGGCVSQWKAAAGFLFCVMVFASAERPVFTNHFLVELHKGGEDKARQVAAEHGFGVRKV
KMALQQEGFDRKKRGYRDINEIDINMNDPLFTKQWYLINTGQADGTPGLDLNVAEAWELG
YTGKGVTIGIMDDGIDYLHPDLASNYNAEASYDFSSNDPYPYPRYTDDWFNSHGTRCAGE
VSAAANNNICGVGVAYNSKVAGIRMLDQPFMTDIIEASSISHMPQLIDIYSASWGPTDNG
KTVDGPRELTLQAMADGVNKGRGGKGSIYVWASGDGGSYDDCNCDGYASSMWTISINSAI
NDGRTALYDESCSSTLASTFSNGRKRNPEAGVATTDLYGNCTLRHSGTSAAAPEAAGVFA
LALEANLGLTWRDMQHLTVLTSKRNQLHDEVHQWRRNGVGLEFNHLFGYGVLDAGAMVKM
AKDWKTVPERFHCVGGSVQDPEKIPSTGKLVLTLTTDACEGKENFVRYLEHVQAVITVNA
TRRGDLNINMTSPMGTKSILLSRRPRDDDSKVGFDKWPFMTTHTWGEDARGTWTLELGFV
GSAPQKGVLKEWTLMLHGTQSAPYIDQVVRDYQSKLAMSKKEELEEELDEAVERSLKSIL
NKN

FIGURE 9C
Isoform 3(P16519-3; NCBI Reference Sequence: NM_001201528.1)
The sequence of this isoform differs from the canonical sequence as follows:
    1-19: Missing.
MVFASAERPVFTNHFLVELHKGGEDKARQVAAEHGFGVRKLPFAEGLYHFYHNGLAKAKR
RRSLHHKQQLERDPRVKMALQQEGFDRKKRGYRDINEIDINMNDPLFTKQWYLINTGQAD
GTPGLDLNVAEAWELGYTGKGVTIGIMDDGIDYLHPDLASNYNAEASYDFSSNDPYPYPR
YTDDWFNSHGTRCAGEVSAAANNNICGVGVAYNSKVAGIRMLDQPFMTDIIEASSISHMP
QLIDIYSASWGPTDNGKTVDGPRELTLQAMADGVNKGRGGKGSIYVWASGDGGSYDDCNC
DGYASSMWTISINSAINDGRTALYDESCSSTLASTFSNGRKRNPEAGVATTDLYGNCTLR
HSGTSAAAPEAAGVFALALEANLGLTWRDMQHLTVLTSKRNQLHDEVHQWRRNGVGLEFN
HLFGYGVLDAGAMVKMAKDWKTVPERFHCVGGSVQDPEKIPSTGKLVLTLTTDACEGKEN
FVRYLEHVQAVITVNATRRGDLNINMTSPMGTKSILLSRRPRDDDSKVGFDKWPFMTTHT
WGEDARGTWTLELGFVGSAPQKGVLKEWTLMLHGTQSAPYIDQVVRDYQSKLAMSKKEEL
EEELDEAVERSLKSILNKN

FIGURE 10

Mouse PCSK2 (uniprot #:P21661)

Amino acid sequence (P21661-1; NCBI Reference Sequence: NM_008792.4):

MEGGCGSQWKAAGFLFCVMVFASAERPVFTNHFLVELHKDGEEEARQVAAEHGFGVRKLP
FAEGLYHFYHNGLAKAKRRRSLHHKRQLERDPRIKMALQQEGFDRKKRGYRDINEIDINM
NDPLFTKQWYLFNTGQADGTPGLDLNVAEAWELGYTGKGVTIGIMDDGIDYLHPDLAYNY
NADASYDFSSNDPYPYPRYTDDWFNSHGTRCAGEVSAAASNNICGVGVAYNSKVAGIRML
DQPFMTDIIEASSISHMPQLIDIYSASWGPTDNGKTVDGPRELTLQAMADGVNKGRGGKG
SIYVWASGDGGSYDDCNCDGYASSMWTISINSAINDGRTALYDESCSSTLASTFSNGRKR
NPEAGVATTDLYGNCTLRHSGTSAAAPEAAGVFALALEANLDLTWRDMQHLTVLTSKRNQ
LHDEVHQWRRNGVGLEFNHLFGYGVLDAGAMVKMAKDWKTVPERFHCVGGSVQNPEKIPP
TGKLVLTLKTNACEGKENFVRYLEHVQAVITVNATRRGDLNINMTSPMGTKSILLSRRPR
DDDSKVGFDKWPFMTTHTWGEDARGTWTLELGFVGSAPQKGLLKEWTLMLHGTQSAPYID
QVVRDYQSKLAMSKKQELEEELDEAVERSLQSILRKN

FIGURE 11A

APOE4

```
                        KVEQAVETEPEPELRQQTEWQSGQRWELALGR  32
FWDYLRWVQTLSEQVQEELLSSQVTQELRALMDETMKELKAYKSELEEQL        82
TPVAEETRARLSKELQAAQARLGADMEDVRGRLVQYRGEVQAMLGQSTEE       132
LRVRLASHLRKLRKRLLRDADDLQKRLAVYQAGAREGAERGLSAIRERLG       182
PLVEQGRVRAATVGSLAGQPLQERAQAWGERLRARMEEMGSRTRDRLDEV       232
KEQVAEVRAKLEEQAQQIRLQAEAFQARLKSWFEPLVEDMQRQWAGLVEK       282
VQAAVGTSAAPVPSDNH                                        299
```

FIGURE 11B

```
  1  mkvlwaallvtflagcqakveqavetepepelrqqtewqsgqrwelalgrfwdylrwvqt
 61  lseqvqeellssqvtqelralmdetmkelkaykseleeqltpvaeetrarlskelqaaqa
121  rlgadmedvrgrlvqyrgevqamlgqsteelrvrlashlrklrkrllrdaddlqkrlavy
181  qagaregaerglsairerlgplveqgrvraatvgslagqplqeraqawgerlrarmeemg
241  srtrdrldevkeqvaevrakleeqaqqirlqaeafqarlkswfeplvedmqrqwaglvek
301  vqaavgtsaapvpsdnh
```

FIGURE 12

APOE3

```
MKVLWAALLVTFLAGCQAKVEQAVETEPEPELRQQTEWQSGQRWELALGR        50
FWDYLRWVQTLSEQVQEELLSSQVTQELRALMDETMKELKAYKSELEEQL       100
TPVAEETRARLSKELQAAQARLGADMEDVCGRLVQYRGEVQAMLGQSTEE       150
LRVRLASHLRKLRKRLLRDADDLQKRLAVYQAGAREGAERGLSAIRERLG       200
PLVEQGRVRAATVGSLAGQPLQERAQAWGERLRARMEEMGSRTRDRLDEV       250
KEQVAEVRAKLEEQAQQIRLQAEAFQARLKSWFEPLVEDMQRQWAGLVEK       300
VQAAVGTSAAPVPSDNH                                        317
```

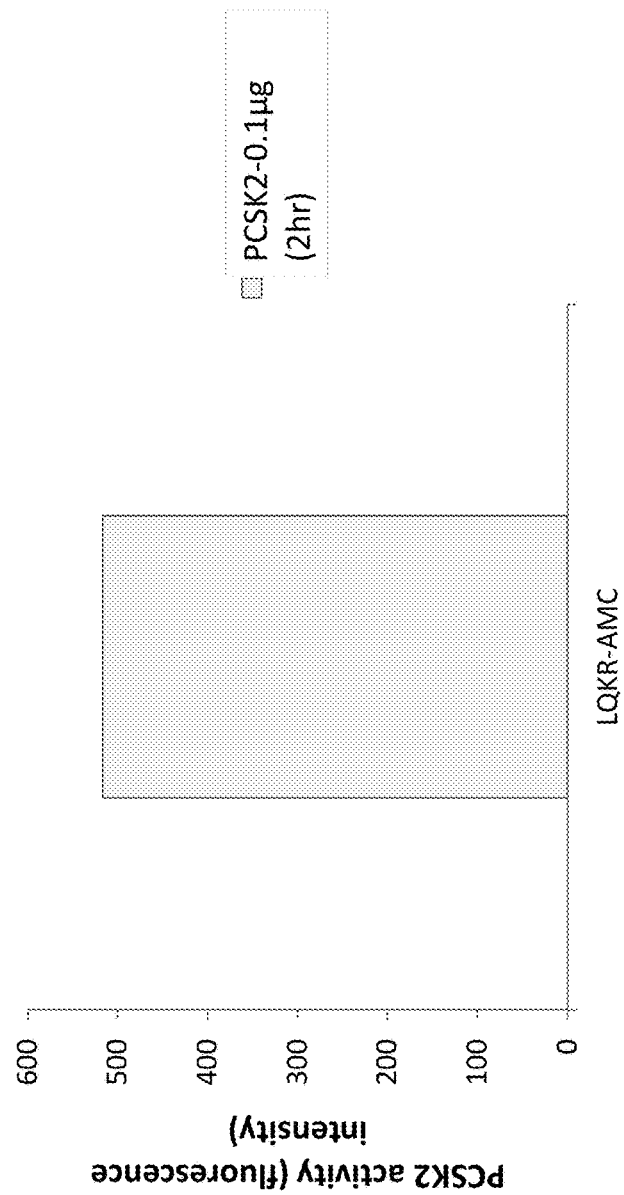

COMPOSITIONS AND METHODS FOR IDENTIFYING AGENTS FOR TREATING APOE-RELATED DISEASES

This application claims the benefit of U.S. Provisional Patent Application No. 62/155,868, filed May 1, 2015, which application is incorporated herein by reference in its entirety.

INTRODUCTION

Alzheimer's disease (AD) is the most common cause of dementia among older people, and the sixth leading cause of death in the United States. Apolipoprotein E (apoE) neuronal specific cleavage, which generates toxic apoE fragments, has been identified as an important molecular mechanism in AD. Higher amounts of apoE fragments were detected in AD brains compared to controls. High levels of neuronal apoE fragmentation are associated with the apoE4 genotype. Toxic apoE fragments lead to neuronal toxicity, cytoskeleton dysregulation, mitochondrial impairment, and memory/learning deficits.

There is a need in the art for methods of identifying inhibitors of enzymes that produce toxic fragments of apoE.

LITERATURE

Pickett et al. (2013) *PLoSOne* 8:e55065; Ozawa et al. (2010) *Endocrinol.* 15:4437; Brecht et al. (2004) *J. Neurosci.* 24:2527; Zhou and Mains (1994) *J. Biol. Chem.* 269: 17440; Frank et al. (2013) *Mol. Genet. Metab.* 110:191; WO 2010/059942

SUMMARY

The present disclosure describes the identification of Protein Convertase, Subtilisin/Kexin-Type-1 and Type-2 (PCSK1 and PCSK2) as apoE-cleaving proteases, which are capable of producing toxic apoE fragments and provides methods of identifying a candidate agent for treating an apoE-associated neurodegenerative disorder. The methods generally involve contacting a PCSK1 or a PCSK2 polypeptide with an apoE polypeptide in the presence of a test agent.

BRIEF DESCRIPTION OF THE DRAWINGS

FIGS. 7A and 7B provide amino acid sequences of human PCSK1. FIG. 7A depicts SEQ ID NO:1; FIG. 7B depicts MERRAWSLQCTAFVLFCAWCALN-SAKAKRQFVNEWAAEIPGGPEAASAIAEELGYDLLG (SEQ ID NO:2), MGKGSISFLFFS (SEQ ID NO:3) and SEQ ID NO:4 (longest sequence).

FIG. 8 provides an amino acid sequence of mouse PCSK1 (SEQ ID NO:5).

FIGS. 9A-9C provide amino acid sequences of human PCSK2 (SEQ ID NOs: 6-8, respectively).

FIG. 10 provides an amino acid sequence of mouse PCSK2 (SEQ ID NO:9).

FIGS. 11A and 11B provide amino acid sequences of apoE4 (SEQ ID NO:10 and SEQ ID NO:11, respectively).

FIG. 12 provides an amino acid sequence of apoE3 (SEQ ID NO:12).

FIG. 14 depicts an in vitro assay of PCSK2 activity using an apoE-derived peptide as a substrate.

DEFINITIONS

Figure 1:
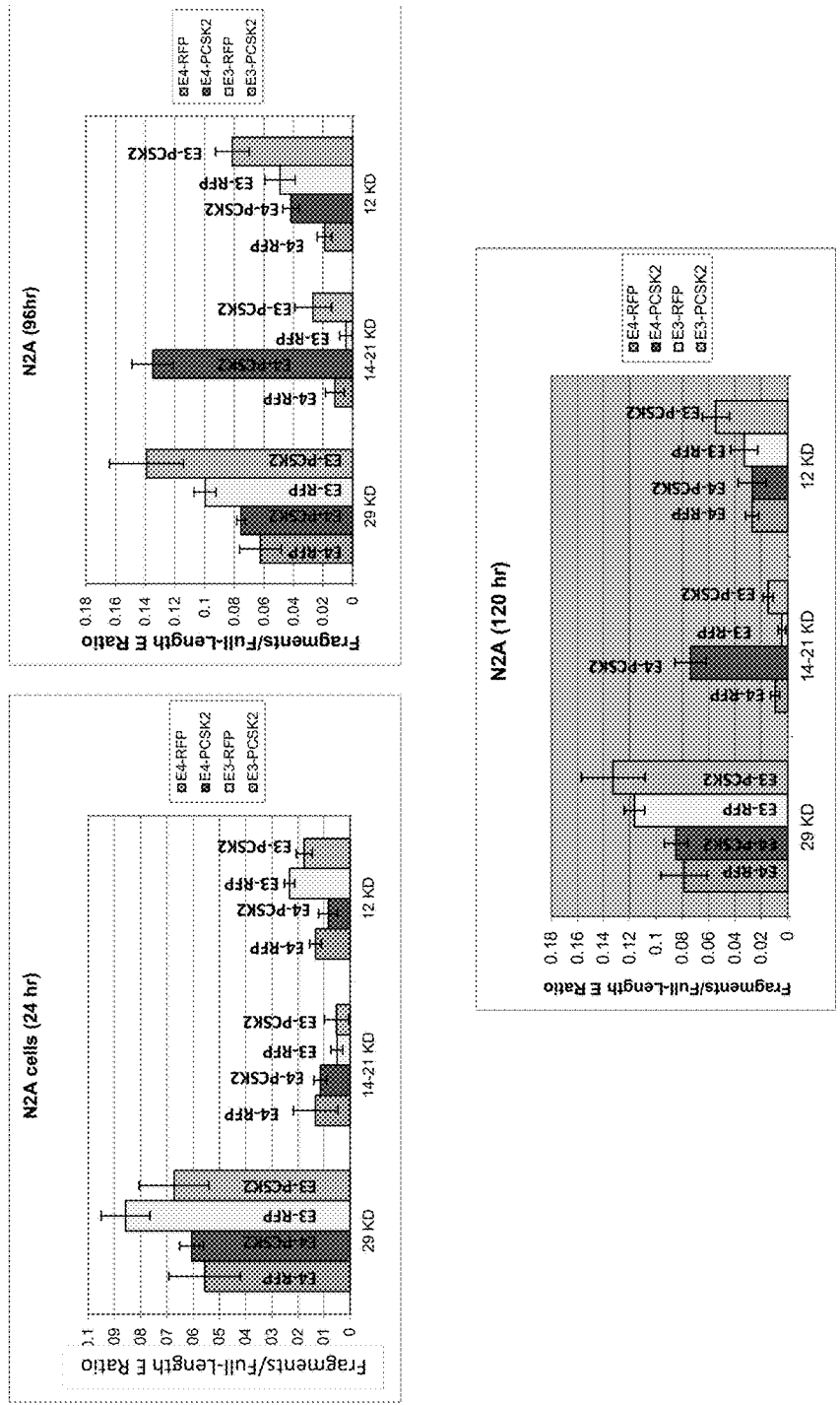
FIG. 1 depicts the effect of overexpression of PCSK2 on generation of apoE fragments (12 kD; 14-21 kD; and 29 kD) in N2A-apoE4 cells and in N2A-apoE3 cells.

The terms "polypeptide," "peptide," and "protein", used interchangeably herein, refer to a polymeric form of amino acids of any length, which can include coded and non-coded amino acids, chemically or biochemically modified or derivatized amino acids, and polypeptides having modified peptide backbones. The term includes fusion proteins, including, but not limited to, fusion proteins with a heterologous amino acid sequence, fusions with heterologous and homologous leader sequences, with or without N-terminal methionine residues; immunologically tagged proteins; and the like. $NH_2$ refers to the free amino group present at the amino terminus of a polypeptide. COOH refers to the free carboxyl group present at the carboxyl terminus of a polypeptide. In keeping with standard polypeptide nomenclature, *J. Biol. Chem.*, 243 (1969), 3552-59 is used.

As used herein, an "apoE-associated disorder" is any disorder that is caused by the presence of apoE or a fragment thereof, such as an apoE fragment as described herein, e.g., an apoE4 fragment as described herein, in a cell, in the serum, in the interstitial fluid, in the cerebrospinal fluid, or in any other bodily fluid of an individual; any physiological process or metabolic event that is influenced by apoE domain interaction; any disorder that is characterized by the presence of apoE or a fragment thereof, such as an apoE fragment as described herein, e.g., an apoE4 fragment as described herein; a symptom of a disorder that is caused by the presence of apoE or a fragment thereof, such as an apoE fragment as described herein, e.g., an apoE4 fragment as described herein, in a cell or in a bodily fluid; a phenomenon associated with a disorder caused by the presence in a cell or in a bodily fluid of apoE or a fragment thereof, such as an apoE fragment as described herein, e.g., an apoE4 fragment as described herein; and the sequelae of any disorder that is caused by the presence of apoE or a fragment thereof, such as an apoE fragment as described herein, e.g., an apoE4 fragment as described herein. ApoE-associated disorders include apoE-associated neurological disorders and disorders related to high serum lipid levels. ApoE-associated neurological disorders include, but are not limited to, sporadic Alzheimer's disease; familial Alzheimer's disease; poor outcome following a stroke; poor outcome following traumatic head injury; and cerebral ischemia. Phenomena associated with apoE-associated neurological disorders include, but are not limited to, neurofibrillary tangles; amyloid deposits; memory loss; and a reduction in cognitive function. ApoE-related disorders associated with high serum lipid levels include, but are not limited to, atherosclerosis, and coronary artery disease. Phenomena associated with such apoE-associated disorders include high serum cholesterol levels.

In some embodiments, an apoE-related disorder is an apoE4-related disorder. As used herein, an "apoE4-associated disorder" is any disorder that is caused by the presence of apoE4 (e.g., an apoE4 fragment as described herein) in a cell, in the serum, in the interstitial fluid, in the cerebrospinal fluid, or in any other bodily fluid of an individual; any physiological process or metabolic event that is influenced by apoE4 domain interaction; any disorder that is characterized by the presence of apoE4 (e.g., an apoE4 fragment as described herein); a symptom of a disorder that is caused by the presence of apoE4 (e.g., an apoE4 fragment as described herein) in a cell or in a bodily fluid; a phenomenon associated with a disorder caused by the presence in a cell or in a bodily fluid of apoE4 (e.g., an apoE4 fragment as described herein); and the sequelae of any disorder that is caused by the presence of apoE4 (e.g., an apoE4 fragment as described herein). ApoE4-associated disorders include apoE4-associated neurological disorders and disorders related to high serum lipid levels. ApoE4-associated neurological disorders include, but are not limited to, sporadic Alzheimer's disease; familial Alzheimer's disease; poor outcome following a stroke; poor outcome following traumatic head injury; and cerebral ischemia. Phenomena associated with apoE4-associated neurological disorders include, but are not limited to, neurofibrillary tangles; amyloid deposits; memory loss; and a reduction in cognitive function. ApoE4-related disorders associated with high serum lipid levels include, but are not limited to, atherosclerosis, and coronary artery disease. Phenomena associated with such apoE4-associated disorders include high serum cholesterol levels.

The term "Alzheimer's disease" (abbreviated herein as "AD") as used herein refers to a condition associated with formation of neuritic plaques comprising amyloid β protein primarily in the hippocampus and cerebral cortex, as well as impairment in both learning and memory. "AD" as used herein is meant to encompass both AD as well as AD-type pathologies.

The term "phenomenon associated with Alzheimer's disease" as used herein refers to a structural, molecular, or functional event associated with AD, particularly such an event that is readily assessable in an animal model. Such events include, but are not limited to, amyloid deposition, neuropathological developments, learning and memory deficits, and other AD-associated characteristics.

Before the present invention is further described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a," "an," and "the" include plural referents unless the context clearly dictates otherwise. Thus, for example, reference to "a PCSK1 polypeptide" includes a plurality of such polypeptides and reference to "the apoE substrate" includes reference to one or more apoE substrates and equivalents thereof known to those skilled in the art, and so forth. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination. All combinations of the embodiments pertaining to the invention are specifically embraced by the present invention and are disclosed herein just as if each and every combination was individually and explicitly disclosed. In addition, all sub-combinations of the various embodiments and elements thereof are also specifically embraced by the present invention and are disclosed herein just as if each and every such sub-combination was individually and explicitly disclosed herein.

The publications discussed herein are provided solely for their disclosure prior to the filing date of the present application. Nothing herein is to be construed as an admission that the present invention is not entitled to antedate such publication. Further, the dates of publication provided may be different from the actual publication dates which may need to be independently confirmed.

DETAILED DESCRIPTION

The present disclosure provides methods of identifying a candidate agent for treating an apoE-associated neurodegenerative disorder. The methods generally involve contacting a PCSK1 or a PCSK2 polypeptide with an apoE substrate for the PCSK1 or PCSK2 polypeptide (e.g., where the apoE substrate is an apoE polypeptide, e.g., a full-length apoE polypeptide, a fragment of an apoE polypeptide, an apoE polypeptide fragment that comprises a fluorophore (e.g., at the C-terminus), etc.) in the presence of a test agent; and determining the effect of the test agent on cleavage of the apoE substrate by the PCSK1 or PCSK2 polypeptide.

Screening Methods

The present disclosure provides methods of identifying a candidate agent for treating an apoE-associated neurodegenerative disorder. The methods generally involve contacting a PCSK1 or a PCSK2 polypeptide with an apoE substrate of a PCSK1 or PCSK2 polypeptide in the presence of a test agent; and determining the effect, if any, of the test agent on cleavage of the apoE substrate by the PCSK1 or PCSK2 polypeptide. In some cases, the substrate is an apoE4 polypeptide. In some cases, the apoE4 polypeptide comprises a fluorophore. In some cases, the apoE4 polypeptide comprises a fluorophore attached (e.g., covalently linked) to the C-terminus of the apoE4 polypeptide. In some cases, the substrate is a full-length apoE4 polypeptide. In some cases, the substrate is a fragment of a full-length apoE4 polypeptide; e.g., the substrate can be an apoE4 polypeptide having a length that is less than a full-length apoE4 polypeptide; e.g., where the apoE4 polypeptide has a length of from 2 amino acids to 300 amino acids, or from 4 amino acids (aa) to 300 aa. In some cases, the substrate is a fragment of an apoE4 polypeptide, where the fragment comprises a fluorophore attached to the C-terminus.

One non-limiting example of a suitable apoE4 polypeptide (for use as a substrate in a screening method of the present disclosure) is a polypeptide comprising the amino acid sequence RLLR (SEQ ID NO:14), and having a length of from 4 aa to 10 aa, from 10 aa to 15 aa, from 15 aa to 20 aa, or from 20 aa to 25 aa. As one example, an apoE4 polypeptide is RLLR (SEQ ID NO:14). In some cases, the apoE4 polypeptide comprises a fluorescent moiety (e.g., 7-amino-4-methyl-coumarin; "AMC"). As one example, an apoE4 polypeptide is RLLR-AMC.

One non-limiting example of a suitable apoE4 polypeptide (for use as a substrate in a screening method of the present disclosure) is a polypeptide comprising the amino acid sequence LQKR (SEQ ID NO:15), and having a length of from 4 aa to 10 aa, from 10 aa to 15 aa, from 15 aa to 20 aa, or from 20 aa to 25 aa. As one example, an apoE4 polypeptide is LQKR (SEQ ID NO:15). In some cases, the apoE4 polypeptide comprises a fluorescent moiety (e.g., 7-amino-4-methyl-coumarin; "AMC"). As one example, an apoE4 polypeptide is LQKR-AMC.

An apoE4 polypeptide can have a length of from 2 amino acids to 320 amino acids, or from 4 amino acids (aa) to 320 aa, e.g., 2 aa, 3 aa, from 4 aa to 10 aa, from 10 aa to 15 aa, from 15 aa to 20 aa, from 20 aa to 25 aa, from 25 aa to 30 aa, from 30 aa to 50 aa, from 50 aa to 75 aa, from 75 aa to 100 aa, from 100 aa to 150 aa, from 150 aa to 200 aa, from 200 aa to 250 aa, from 250 aa to 300 aa, or from 300 aa to 320 aa.

A test agent that inhibits cleavage of the apoE substrate is considered a candidate agent for treating an apoE-associated neurodegenerative disorder. For example, a test agent that inhibits PCSK1-mediated or PCSK2-mediated cleavage of the apoE substrate by at least about 10%, at least about 20%, at least about 25%, at least about 30%, at least about 35%, Whether a test agent inhibits PCSK1- or PCSK2-mediated cleavage of an apoE substrate to generate neurotoxic apoE fragments can be determined using any convenient method. For example, generation of apoE fragments can be detected by protein blot, mass spectrometry, enzyme-linked immunosorbant assay (ELISA), or any other convenient method.

In some cases, e.g., when full-length apoE polypeptide (e.g., full-length apoE4 polypeptide) is used as the substrate, apoE fragments generated by action of a PCSK1 or a PCSK2 polypeptide have a molecular weight of about 29 kD. In some cases, apoE fragments generated by action of a PCSK1 or a PCSK2 polypeptide have a molecular weight of 14 kD to 21 kD. In some cases, apoE fragments generated by action of a PCSK1 or a PCSK2 polypeptide have a molecular weight of about 12 kD.

In some cases, e.g., when a fluorescently labeled apoE polypeptide (e.g., apoE4 polypeptide) is used as a substrate, cleavage by PCSK1 or PCSK2 polypeptide generates a fluorescent signal. Thus, in these cases, apoE fragments generated by action of a PCSK1 or a PCSK2 polypeptide can be detected by detecting fluorescence, e.g., using a fluorescence detection device such as a fluorescent plate reader.

Neurotoxic apoE3 fragments that can be generated by action of a PCSK1 or a PCSK2 polypeptide include, but are not limited to, carboxyl-terminal truncated apoE3. In some cases, neurotoxic apoE3 fragments include at least amino acids 244-260 of apoE3. Neurotoxic apoE3 fragments include carboxyl-terminal truncated apoE3 that binds p-tau and phosphorylated neurofilament (p-NF). Neurotoxic apoE4 fragments that can be generated by action of a PCSK1 or a PCSK2 polypeptide include, but are not limited to, carboxyl-terminal truncated apoE4. In some cases, neurotoxic apoE4 fragments include at least amino acids 244-260 of apoE4. Neurotoxic apoE4 fragments include carboxyl-terminal truncated apoE4 that binds p-tau and phosphorylated neurofilament (p-NF). Additional description of neurotoxic apoE fragments is provided in U.S. Pat. Nos. 6,787,519, and 7,682,795, the disclosure of each of which is incorporated by reference herein.

Specific neurotoxic carboxyl-terminal truncated apoE4 polypeptides that give rise to neurofibrillary tangles include, but are not limited to, apoE4Δ272-299; apoE4Δ261-299; and apoE4Δ252-299, based on the numbering of the apoE4 amino acid sequence provided in FIG. 11A and as follows:

```
                                                         (SEQ ID NO: 10)
KVEQAVETEPEPELRQQTEWQSGQRWELALGR                                      32

FWDYLRWVQTLSEQVQEELLSSQVTQELRALMDETMKELKAYKSELEEQL                    82

TPVAEETRARLSKELQAAQARLGADMEDVRGRLVQYRGEVQAMLGQSTEE                   132

LRVRLASHLRKLRKRLLRDADDLQKRLAVYQAGAREGAERGLSAIRERLG                   182

PLVEQGRVRAATVGSLAGQPLQERAQAWGERLRARMEEMGSRTRDRLDEV                   232

KEQVAEVRAKLEEQAQQIRLQAEAFQARLKSWFEPLVEDMQRQWAGLVEK                   282

VQAAVGTSAAPVPSDNH                                                    299
``` at least about 40%, at least about 45%, at least about 50%, at least about 55%, at least about 60%, at least about 65%, at least about 70%, at least about 80%, or at least about 90%, compared to a control in the absence of the test agent, is considered a candidate agent for treating an apoE-associated neurodegenerative disorder.

Specific neurotoxic carboxyl-terminal truncated apoE3 polypeptides that give rise to neurofibrillary tangles include, but are not limited to, apoE3Δ272-299, based on the numbering of the apoE3 amino acid sequence provided as follows, which is the mature form of the polypeptide of FIG. 12:

```
                                                        (SEQ ID NO: 13)
KVEQAVETEPEPELRQQTEWQSGQRWELALGR                                     32

FWDYLRWVQTLSEQVQEELLSSQVTQELRALMDETMKELKAYKSELEEQL                   82

TPVAEETRARLSKELQAAQARLGADMEDVCGRLVQYRGEVQAMLGQSTEE                  132

LRVRLASHLRKLRKRLLRDADDLQKRLAVYQAGAREGAERGLSAIRERLG                  182

PLVEQGRVRAATVGSLAGQPLQERAQAWGERLRARMEEMGSRTRDRLDEV                  232

KEQVAEVRAKLEEQAQQIRLQAEAFQARLKSWFEPLVEDMQRQWAGLVEK                  282

VQAAVGTSAAPVPSDNH                                                   299
```

Human apolipoprotein (apo) E, a 34-kDa protein with 299 amino acids (mature form), has three major isoforms, apoE2, apoE3, and apoE4. Amino acid sequences of apoE polypeptides of various mammalian species are known in the art. See, e.g., Rall et al. (1982) *J. Biol. Chem.* 257:4171; Weisgraber (1994) *Adv. Protein Chem.* 45:249-302; GenBank NP_000032.

An "apoE4 polypeptide" can comprise an amino acid sequence having at least about 75%, at least about 80%, at least about 90%, at least about 95%, at least about 98%, at least about 99%, or 100%, amino acid sequence identity to a contiguous stretch of from about 100 amino acids (aa) to about 125 aa, from about 125 aa to about 150 aa, from about 150 aa to about 175 aa, from about 175 aa to about 200 aa, from about 200 aa to about 225 aa, from about 225 aa to about 250 aa, from about 250 aa to about 275 aa, or from about 275 aa to about 299 aa, of amino acids 19-317 of the apoE4 amino acid sequence depicted in FIG. 11B (SEQ ID NO:11). An "apoE4 polypeptide" can comprise an amino acid sequence having at least about 75%, at least about 80%, at least about 90%, at least about 95%, at least about 98%, at least about 99%, or 100%, amino acid sequence identity to a contiguous stretch of from about 100 amino acids (aa) to about 125 aa, from about 125 aa to about 150 aa, from about 150 aa to about 175 aa, from about 175 aa to about 200 aa, from about 200 aa to about 225 aa, from about 225 aa to about 250 aa, from about 250 aa to about 275 aa, or from about 275 aa to about 299 aa, of the apoE4 amino acid sequence depicted in FIG. 11A.

An "apoE3 polypeptide" can comprise an amino acid sequence having at least about 75%, at least about 80%, at least about 90%, at least about 95%, at least about 98%, at least about 99%, or 100%, amino acid sequence identity to a contiguous stretch of from about 100 amino acids (aa) to about 125 aa, from about 125 aa to about 150 aa, from about 150 aa to about 175 aa, from about 175 aa to about 200 aa, from about 200 aa to about 225 aa, from about 225 aa to about 250 aa, from about 250 aa to about 275 aa, or from about 275 aa to about 299 aa, of amino acids 19-317 of the apoE3 amino acid sequence depicted in FIG. 12 (SEQ ID NO:12).

A PCSK1 polypeptide preferentially cleaves apoE4. For example, a PCSK1 polypeptide cleaves apoE4, but does not substantially cleave apoE3. A PCSK2 polypeptide preferentially cleaves apoE4. For example, a PCSK2 polypeptide cleaves apoE4, but does not substantially cleave apoE3.

In some cases, a test agent of interest selectively inhibits PCSK1- and/or PCSK2-mediated cleavage of apoE4. For example, in some embodiments, a test agent of interest selectively inhibits enzymatic activity of PCSK1, but does not substantially inhibit enzymatic activity of a non-PCSK1 enzyme (e.g., a serine protease other than PCSK1), e.g., the test agent of interest inhibits a non-PCSK1 enzyme, if at all, by no more than about 15%, e.g., by less than 15%, less than 10%, less than 5%, or less than 1%.

An apoE substrate for use in a subject method can be a full-length apoE polypeptide, or a fragment of an apoE polypeptide. In some cases, the apoE substrate is full-length apoE4. In some cases, an apoE substrate is an apoE polypeptide comprising an amino acid sequence having at least about 75%, at least about 80%, at least about 90%, at least about 95%, at least about 98%, at least about 99%, or 100%, amino acid sequence identity to a contiguous stretch of from about 100 amino acids (aa) to about 125 aa, from about 125 aa to about 150 aa, from about 150 aa to about 175 aa, from about 175 aa to about 200 aa, from about 200 aa to about 225 aa, from about 225 aa to about 250 aa, from about 250 aa to about 275 aa, or from about 275 aa to about 299 aa, of amino acids 19-317 of the apoE4 amino acid sequence depicted in FIG. 11B (SEQ ID NO:11). In some cases, an apoE substrate is an apoE polypeptide comprising an amino acid sequence having at least about 75%, at least about 80%, at least about 90%, at least about 95%, at least about 98%, at least about 99%, or 100%, amino acid sequence identity to a contiguous stretch of from about 100 amino acids (aa) to about 125 aa, from about 125 aa to about 150 aa, from about 150 aa to about 175 aa, from about 175 aa to about 200 aa, from about 200 aa to about 225 aa, from about 225 aa to about 250 aa, from about 250 aa to about 275 aa, or from about 275 aa to about 299 aa, of the apoE4 amino acid sequence depicted in FIG. 11A. In some cases, the apoE substrate is an apoE polypeptide (e.g., an apoE4 polypeptide) having a length of from 2 amino acids to 320 amino acids, or from 4 amino acids (aa) to 320 aa, e.g., 2 amino acids, 3 amino acids, from 4 aa to 10 aa, from 10 aa to 15 aa, from 15 aa to 20 aa, from 20 aa to 25 aa, from 25 aa to 30 aa, from 30 aa to 50 aa, from 50 aa to 75 aa, from 75 aa to 100 aa, from 100 aa to 150 aa, from 150 aa to 200 aa, from 200 aa to 250 aa, from 250 aa to 300 aa, or from 300 aa to 320 aa. In some cases, the apoE substrate is an apoE polypeptide (e.g., an apoE4 polypeptide) having a length of from 4 amino acids (aa) to 25 amino acids; e.g., the apoE substrate is an apoE polypeptide (e.g., an apoE4 polypeptide) having a length of 4, 5, 6, 7, 8, 9, 10, 11, 12, 13, 14, 15, 16, 17, 18, 19, 20, 21, 22, 23, 24, or 25 amino acids. In some cases, the apoE substrate is an apoE polypeptide (e.g., an apoE4 polypeptide) having a length of from 4 amino acids (aa) to 25 amino acids; e.g., the apoE substrate is an apoE polypeptide (e.g., an apoE4 polypeptide) having a length of 4, 5, 6, 7, 8, 9, 10, 11, 12, 13, 14, 15, 16, 17, 18, 19, 20, 21, 22, 23, 24, or 25 amino acids; where the apoE polypeptide (e.g., the apoE4 polypeptide) comprises a fluorescent moiety (e.g., where the fluorescent moiety is covalently linked to the apoE4 polypeptide). In some cases, the apoE substrate is an apoE polypeptide (e.g., an apoE4 polypeptide) having a length of from 4 amino acids (aa) to 25 amino acids; e.g., the apoE substrate is an apoE polypeptide (e.g., an apoE4 polypeptide) having a length of 4, 5, 6, 7, 8, 9, 10, 11, 12, 13, 14, 15, 16, 17, 18, 19, 20, 21, 22, 23, 24, or 25 amino acids; where the apoE polypeptide (e.g., the apoE4 polypeptide) comprises a 7-amino-4-methyl-coumarin moiety.

In some embodiments, a suitable apoE substrate is fluorogenic. For example, an apoE polypeptide can be conjugated to a fluorescent moiety, forming an apoE polypeptide-fluorescent moiety conjugate, such that, when conjugated to the apoE polypeptide, the fluorescent moiety does not produce a fluorescent signal, e.g., the fluorescence is quenched, and such that, when the apoE polypeptide-fluorescent moiety conjugate is cleaved by PCSK1 or PCSK2, the fluorescent moiety is released and produces a fluorescent signal. A non-limiting example of such a moiety is 7-amino-4-methyl-coumarin (AMC).

In some cases, the method is an in vitro cell-free method. Cell-free methods generally involve contacting an isolated (e.g., purified) PCSK1 or PCSK2 polypeptide with a test agent and an apoE substrate, and determining the effect, if any, of the test agent on the enzymatic activity of the PCSK1 or PCSK2 polypeptide. Purified PCSK1 or PCSK2 polypeptides include PCSK1 or PCSK2 polypeptides that are at least 75% pure, at least 80% pure, at least 85% pure, at least 90% pure, at least 95% pure, or at least 98% pure, e.g., at least 75%, at least 80%, at least 85%, at least 90%, at least 95%, free of other (non-PCSK1 or PCSK2) proteins, other macromolecules (other than the apoE substrate), or other contaminants. PCSK1 and PCSK2 polypeptides are described above. A subject cell-free in vitro assay can also be carried out with a cell lysate, e.g., a lysate of a primary neuron, or other cell that synthesizes PCSK1 or PCSK2; a lysate of a genetically modified cell that is genetically modified with a nucleic acid(s) comprising nucleotide sequences encoding PCSK1 or PCSK2.

A suitable PCSK1 polypeptide comprises an amino acid sequence having at least about 75%, at least about 80%, at least about 90%, at least about 95%, at least about 98%, at least about 99%, or 100%, amino acid sequence identity to the amino acid sequence depicted in any one of FIGS. 7A, 7B, and 8.

A suitable PCSK2 polypeptide comprises an amino acid sequence having at least about 75%, at least about 80%, at least about 90%, at least about 95%, at least about 98%, at least about 99%, or 100%, amino acid sequence identity to the amino acid sequence depicted in any one of FIGS. 9A, 9B, 9C, and 10.

In some cases, the method is an in vitro cell-based method. Cell-based methods generally involve contacting a cell in vitro that produces a PCSK1 or PCSK2 polypeptide with a test agent and an apoE substrate, and determining the effect, if any, of the test agent on the level and/or activity of the PCSK1 or PCSK2 polypeptide in the cell. Where the assay is an in vitro cell-based assay, any of a variety of cells can be used. The cells used in the assay are usually eukaryotic cells, including, but not limited to, rodent cells, human cells, and yeast cells. Suitable cells include mammalian cells adapted to in vitro cell culture. The cells may be primary cell cultures or may be immortalized cell lines. The cells may be "recombinant," e.g., the cell may have transiently or stably introduced therein one or more constructs (e.g., a plasmid, a recombinant viral vector, or any other suitable vector) that comprise a nucleotide sequence encoding a PCSK1 or PCSK2 polypeptide, and a nucleotide sequence encoding an apoE substrate. The nucleotide sequence encoding a PCSK1 or PCSK2 polypeptide can be operably linked to a transcriptional control element, e.g., a neuron-specific promoter.

Neuron-specific promoters and other control elements (e.g., enhancers) are known in the art. Suitable neuron-specific control sequences include, but are not limited to, a neuron-specific enolase (NSE) promoter (see, e.g., EMBL HSENO2, X51956); an aromatic amino acid decarboxylase (AADC) promoter; a neurofilament promoter (see, e.g., GenBank HUMNFL, L04147); a synapsin promoter (see, e.g., GenBank HUMSYNIB, M55301); a thy-1 promoter (see, e.g., Chen et al. (1987) *Cell* 51:7-19); a serotonin receptor promoter (see, e.g., GenBank S62283); a tyrosine hydroxylase promoter (TH) (see, e.g., *Nucl. Acids. Res.* 15:2363-2384 (1987) and *Neuron* 6:583-594 (1991)); a GnRH promoter (see, e.g., Radovick et al., *Proc. Natl. Acad. Sci. USA* 88:3402-3406 (1991)); an L7 promoter (see, e.g., Oberdick et al., *Science* 248:223-226 (1990)); a DNMT promoter (see, e.g., Bartge et al., *Proc. Natl. Acad. Sci. USA* 85:3648-3652 (1988)); an enkephalin promoter (see, e.g., Comb et al., *EMBO J.* 17:3793-3805 (1988)); a myelin basic protein (MBP) promoter; and a CMV enhancer/platelet-derived growth factor-β promoter (see, e.g., Liu et al. (2004) *Gene Therapy* 11:52-60).

The cell can be any mammalian cell, including a primary cell, a mammalian cell line, etc. Suitable mammalian cells include primary cells and immortalized cell lines. Suitable mammalian cell lines include human cell lines, non-human primate cell lines, rodent (e.g., mouse, rat) cell lines, and the like. Suitable mammalian cell lines include, but are not limited to, HeLa cells (e.g., American Type Culture Collection (ATCC) No. CCL-2), CHO cells (e.g., ATCC Nos. CRL9618, CCL61, CRL9096), 293 cells (e.g., ATCC No. CRL-1573), Vero cells, NIH 3T3 cells (e.g., ATCC No. CRL-1658), Huh-7 cells, BHK cells (e.g., ATCC No. CCL10), PC12 cells (ATCC No. CRL1721), COS cells, COS-7 cells (ATCC No. CRL1651), RAT1 cells, mouse L cells (ATCC No. CCLI.3), human embryonic kidney (HEK) cells (ATCC No. CRL1573), HLHepG2 cells, and the like.

In some embodiments, the cell is a neuronal cell or a neuronal-like cell. The cells can be of human, non-human primate, mouse, or rat origin, or derived from a mammal other than a human, non-human primate, rat, or mouse. Suitable cell lines include, but are not limited to, a human glioma cell line, e.g., SVGp12 (ATCC CRL-8621), CCF-STTG1 (ATCC CRL-1718), SW 1088 (ATCC HTB-12), SW 1783 (ATCC HTB-13), LLN-18 (ATCC CRL-2610), LNZTA3WT4 (ATCC CRL-11543), LNZTA3WT11 (ATCC CRL-11544), U-138 MG (ATCC HTB-16), U-87 MG (ATCC HTB-14), H4 (ATCC HTB-148), and LN-229 (ATCC CRL-2611); a human medulloblastoma-derived cell line, e.g., D342 Med (ATCC HTB-187), Daoy (ATCC HTB-186), D283 Med (ATCC HTB-185); a human tumor-derived neuronal-like cell, e.g., PFSK-1 (ATCC CRL-2060), SK-N-DZ (ATCCCRL-2149), SK-N-AS (ATCC CRL-2137), SK-N-FI (ATCC CRL-2142), IMR-32 (ATCC CCL-127), etc.; a mouse neuronal cell line, e.g., BC3H1 (ATCC CRL-1443), EOC1 (ATCC CRL-2467), C8-D30 (ATCC CRL-2534), C8-S (ATCC CRL-2535), Neuro-2a (ATCC CCL-131), NB41A3 (ATCC CCL-147), SW10 (ATCC CRL-2766), NG108-15 (ATCC HB-12317); a rat neuronal cell line, e.g., PC-12 (ATCC CRL-1721), CTX TNA2 (ATCC CRL-2006), C6 (ATCC CCL-107), F98 (ATCC CRL-2397), RG2 (ATCC CRL-2433), B35 (ATCC CRL-2754), R3 (ATCC CRL-2764), SCP (ATCC CRL-1700), OA1 (ATCC CRL-6538).

As used herein, the term "determining" refers to both quantitative and qualitative determinations and as such, the term "determining" is used interchangeably herein with "assaying," "measuring," and the like.

The terms "candidate agent," "test agent," "agent", "substance" and "compound" are used interchangeably herein. Candidate agents encompass numerous chemical classes, typically synthetic, semi-synthetic, or naturally occurring inorganic or organic molecules. Candidate agents include those found in large libraries of synthetic or natural compounds. For example, synthetic compound libraries are commercially available from Maybridge Chemical Co. (Trevillet, Cornwall, UK), ComGenex (South San Francisco, Calif.), and MicroSource (New Milford, Conn.). A rare chemical library is available from Aldrich (Milwaukee, Wis.) and can also be used. Alternatively, libraries of natural compounds in the form of bacterial, fungal, plant and animal extracts are available from Pan Labs (Bothell, Wash.) or are readily producible.

Candidate agents may be small organic or inorganic compounds having a molecular weight of more than 50 and less than about 10,000 daltons, e.g., a candidate agent may have a molecular weight of from about 50 daltons to about 100 daltons, from about 100 daltons to about 150 daltons, from about 150 daltons to about 200 daltons, from about 200 daltons to about 500 daltons, from about 500 daltons to about 1000 daltons, from about 1,000 daltons to about 2,500 daltons, from about 2,500 daltons to about 5,000 daltons, from about 5,000 daltons to about 7,500 daltons, or from about 7,500 daltons to about 10,000 daltons. Candidate agents may comprise functional groups necessary for structural interaction with proteins, particularly hydrogen bonding, and may include at least an amine, carbonyl, hydroxyl or carboxyl group, and may contain at least two of the functional chemical groups. The candidate agents may comprise cyclical carbon or heterocyclic structures and/or aromatic or polyaromatic structures substituted with one or more of the above functional groups. Candidate agents are also found among biomolecules including peptides, saccharides, fatty acids, steroids, purines, pyrimidines, derivatives, structural analogs or combinations thereof.

Assays of the invention include controls, where suitable controls include a sample (e.g., a sample comprising a PCSK1 polypeptide or a PCSK2 polypeptide and an apoE substrate for the PCSK1 polypeptide or the PCSK2 polypeptide) in the absence of the test agent. Generally a plurality of assay mixtures is run in parallel with different agent concentrations to obtain a differential response to the various concentrations. Typically, one of these concentrations serves as a negative control, i.e. at zero concentration or below the level of detection.

A variety of other reagents may be included in the screening assay. These include reagents like salts, neutral proteins, e.g. albumin, detergents, etc., that are used to facilitate optimal protein-protein binding and/or reduce non-specific or background interactions. Reagents that improve the efficiency of the assay, such as protease inhibitors, nuclease inhibitors, anti-microbial agents, etc. may be used. The components of the assay mixture are added in any order that provides for the requisite binding or other activity. Incubations are performed at any suitable temperature, typically between 4° C. and 40° C. Incubation periods are selected for optimum activity, but may also be optimized to facilitate rapid high-throughput screening. Typically between 0.1 and 1 hour will be sufficient.

The screening methods may be designed a number of different ways, where a variety of assay configurations and protocols may be employed, as are known in the art. For example, one of the components may be bound to a solid support, and the remaining components contacted with the support bound component. The above components of the method may be combined at substantially the same time or at different times.

A candidate agent can be assessed for any cytotoxic activity it may exhibit toward the cell used in the assay, using well-known assays, such as trypan blue dye exclusion, an MTT (3-(4,5-dimethylthiazol-2-yl)-2,5-diphenyl-2H-tetrazolium bromide) assay, and the like. Agents that do not exhibit cytotoxic activity are considered suitable candidate agents.

In some embodiments, a test agent of interest has a half maximal inhibitory concentration ($IC_{50}$) of from about 0.1 nM to about 1 mM, e.g., from about 0.1 nM to about 0.5 nM, from about 0.5 nM to about 1 nM, from about 1 nM to about 10 nM, from about 10 nM to about 15 nM, from about 15 nM to about 25 nM, from about 25 nM to about 50 nM, from about 50 nM to about 75 nM, from about 75 nM to about 100 nM, from about 100 nM to about 150 nM, from about 150 nM to about 200 nM, from about 200 nM to about 250 nM, from about 250 nM to about 300 nM, from about 300 nM to about 350 nM, from about 350 nM to about 400 nM, from about 400 nM to about 450 nM, from about 450 nM to about 500 nM, from about 500 nM to about 750 nM, from about 750 nM to about 1 µM, from about 1 µM to about 10 µM, from about 10 µM to about 25 µM, from about 25 µM to about 50 µM, from about 50 µM to about 75 µM, from about 75 µM to about 100 µM, from about 100 µM to about 250 µM, from about 250 µM to about 500 µM, or from about 500 µM to about 1 mM.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Celsius, and pressure is at or near atmospheric. Standard abbreviations may be used, e.g., bp, base pair(s); kb, kilobase(s); pl, picoliter(s); s or sec, second(s); min, minute(s); h or hr, hour(s); aa, amino acid(s); kb, kilobase(s); bp, base pair(s); nt, nucleotide(s); i.m., intramuscular(ly); i.p., intraperitoneal (ly); s.c., subcutaneous(ly); and the like.

Example 1: PCSK1 and PCSK2 Play a Role in Generation of Neuronal apoE Fragments

Identifying the protease(s) responsible for apoE cleavage (apoE cleavage enzyme, AECE) in neurons has great academic and therapeutic value. To identify AECE, a panel of serine protease and protease inhibitors was overexpressed in N2A cells (a mouse neuroblastoma cell line) stably expressing human apoE4. Among these candidates, only PCSK1 and PCSK2 overexpression led to an increase of apoE fragmentation with similar cleavage patterns as seen in NSE-apoE4 mouse (apoE4 transcription controlled by a neuron-specific enolase (NSE) promoter) brains and in AD brains.

PCSK1 and PCSK2 belong to a family of nine secretory serine proteases that are related to bacterial subtilisin and yeast kexin. Both enzymes have neuron specific expression patterns in the brain.

ApoE4 generates more fragments than apoE3 in AD brains, suggesting that AECE have a preference of apoE4 over apoE3 as a substrate. It was tested if PCSK1 and PCSK2 have a preference of apoE4 over apoE3 as a substrate. When PCSK1 or PCSK2 was overexpressed in N2A-apoE4 cells (neuroblastoma N2A cells expressing apoE4) and N2A-apoE3 cells (neuroblastoma N2A cells expressing apoE3) via transient transfection, both enzymes generated more apoE fragments in apoE4 stable cells, which correlate with the apoE fragmentation in vivo. The data are depicted in FIG. 1. A mild increase of apoE fragmentation was also detected in NSE-apoE4 primary neurons overexpressing PCSK1 or PCSK2.

Figure 2:
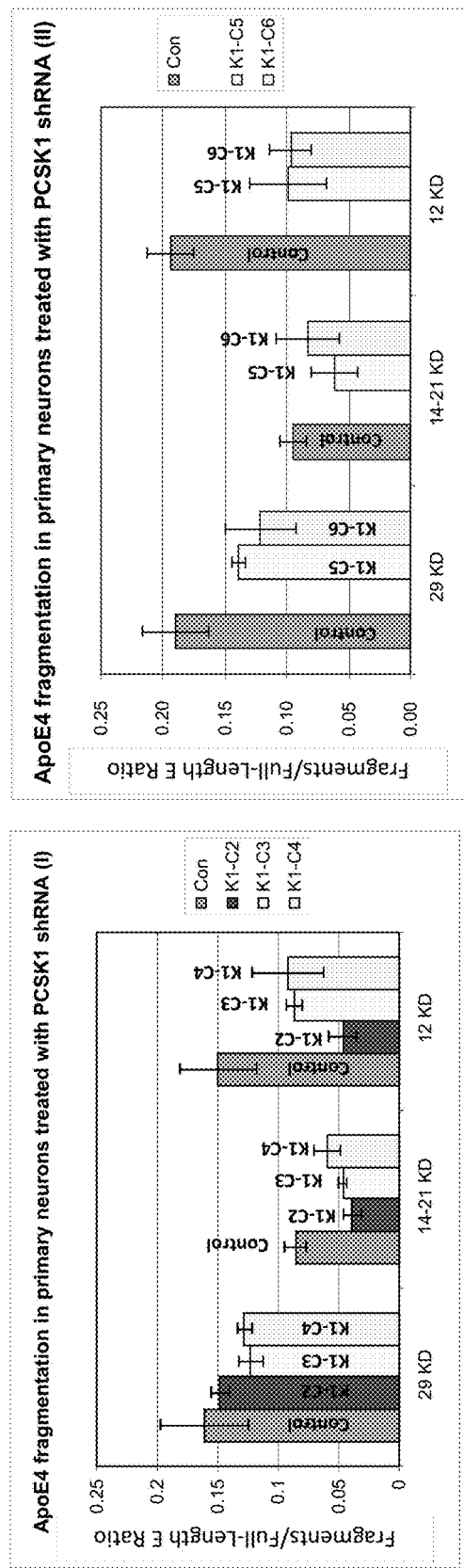
FIG. 2 depicts the effect of PCSK1-specific shRNAs on apoE fragmentation in apoE4 primary neurons.
Figure 3:
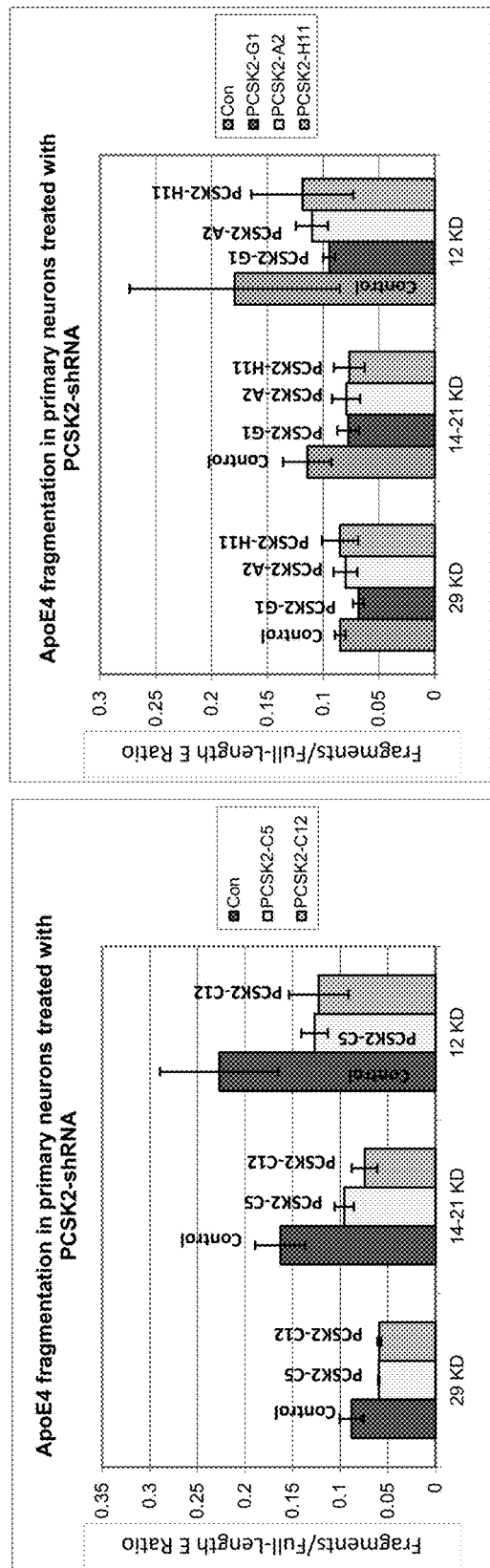
FIG. 3 depicts the effect of PCSK2-specific shRNAs on apoE fragmentation in apoE4 primary neurons.
Figure 4:
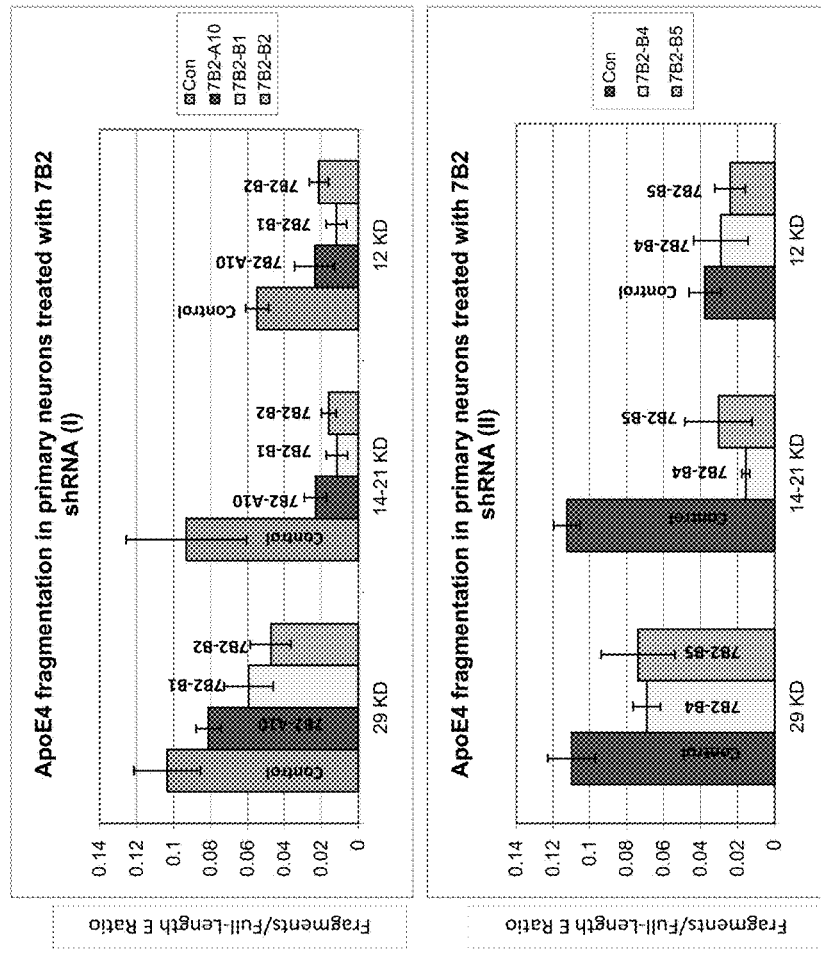
FIG. 4 depicts the effect of 7B2-specific shRNAs on apoE fragmentation in apoE4 primary neurons.

Primary neurons from NSE-apoE4 transgenic mice (NSE-apoE4 primary neurons) generate signature apoE fragmentation as seen in vivo. To confirm that PCSK1 and PCSK2 actually contribute to neuronal cleavage of apoE observed in NSE-apoE4 primary neurons, NSE-apoE4 primary neurons were treated with lentivirus encoding either PCSK1 shRNA or PCSK2 shRNA to decrease the endogenous PCSK1 or PCSK2 levels. As shown in FIGS. 2 and 3, it was observed that knocking down either PCSK1 or PCSK2 in NSE-apoE4 primary neurons decreased apoE fragmentation. Moreover, as shown in FIG. 4, when 7B2, an activator essential for PCSK2 activity, was knocked down in NSE-apoE4 primary neurons, a significant decrease of apoE fragmentation was observed, which also supported the conclusion that PCSK1 and/or PCSK2 are responsible for neuronal apoE cleavage.

Activity of both PCSK1 and PCSK2 is pH and calcium dependent. The optimum pH for PCSK1 and PCSK2 was acidic (pH 6.0 for PCSK1, pH 5.0 for PCSK2). Their activities were enriched in Golgi/trans-Golgi in neurons, which have an acidic environment. Based on this knowledge, it was hypothesized that changing the Golgi pH or calcium levels in neurons would affect PCSK1/PCSK2 activity and further regulate apoE fragmentation. To test this idea, NSE-apoE4 primary neurons were treated with Bafilomycin A, a compound that can increase Golgi pH, or Thapsigargin/2-APB, which can affect the calcium concentration in different cellular compartments. As expected, a decrease of apoE fragmentation was observed after treatment with either compound, providing additional evidence that PCSK1/PCSK2 are responsible for neuronal apoE cleavage.

PCSK1/PCSK2 generated similar apoE fragmentation patterns in N2A-apoE4 cells compared to NSE-apoE4 primary neurons. To determine whether PCSK1/PCSK2-generated apoE fragments are the same as those generated endogenously, lysates from N2A-apoE4 cells overexpressing either PCSK1 or PCSK2, lysates from NSE-apoE4 primary neurons, and the mixture of these two lysates, were tested. ApoE fragmentation was detected by western blot. Most of the apoE fragments aligned among all samples, indicating that the majority of apoE fragments generated by PCSK1/PCSK2 are identical to those generated endogenously.

Figure 5:
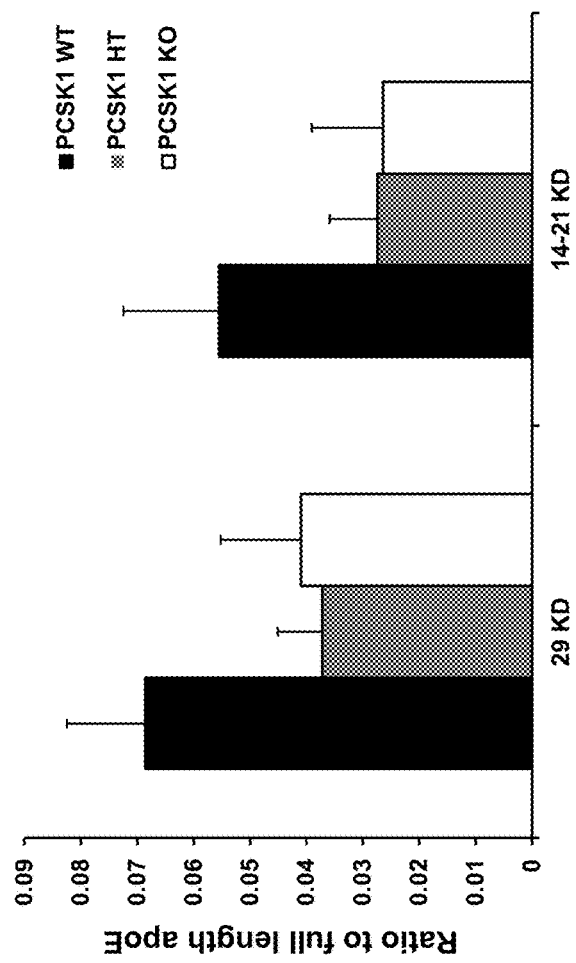
FIG. 5 depicts apoE fragments in brains of PCSK1 knockout mice.

To determine whether PCSK1 contributes to neuronal apoE fragmentation in vivo, NSE-apoE4 mice were bred with a PCSK1 null mouse to obtain offspring expressing apoE4 in neurons with various PCSK1 genotypes (WT, HT, KO). Brains from new born pups were collected and apoE fragmentation was detected by western blot. As shown in FIG. 5, a significant decrease in apoE fragmentation was observed in PCSK1 null, NSE-apoE4 brains compared to that of PCSK1 WT, NSE-apoE4 brains. In addition, primary neurons expressing apoE with various PCSK1 genotypes were cultured. A decrease of apoE fragmentation was observed in PCSK1 null primary neurons compared to PCSK1 wild-type (WT) neurons. All these results suggested that PCSK1 play a role in neuronal apoE fragmentation in vivo.

Figure 6A:
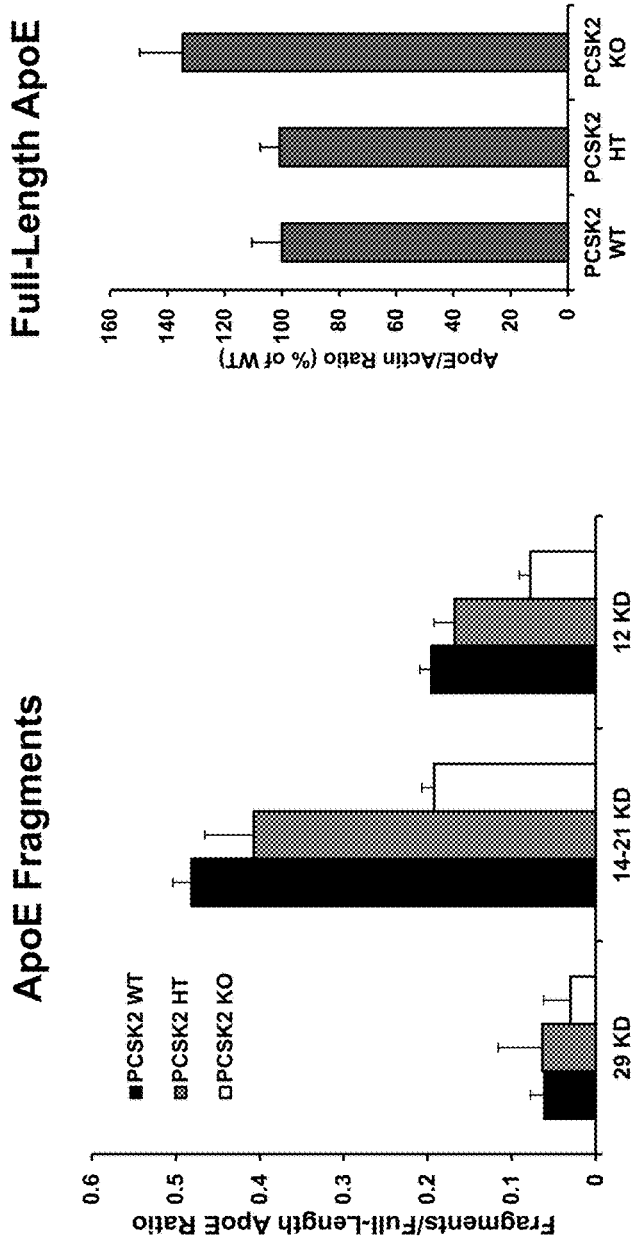
FIGS. 6A and 6B depicts apoE fragments in brains of PCSK2 knockout mice.
Figure 6B:
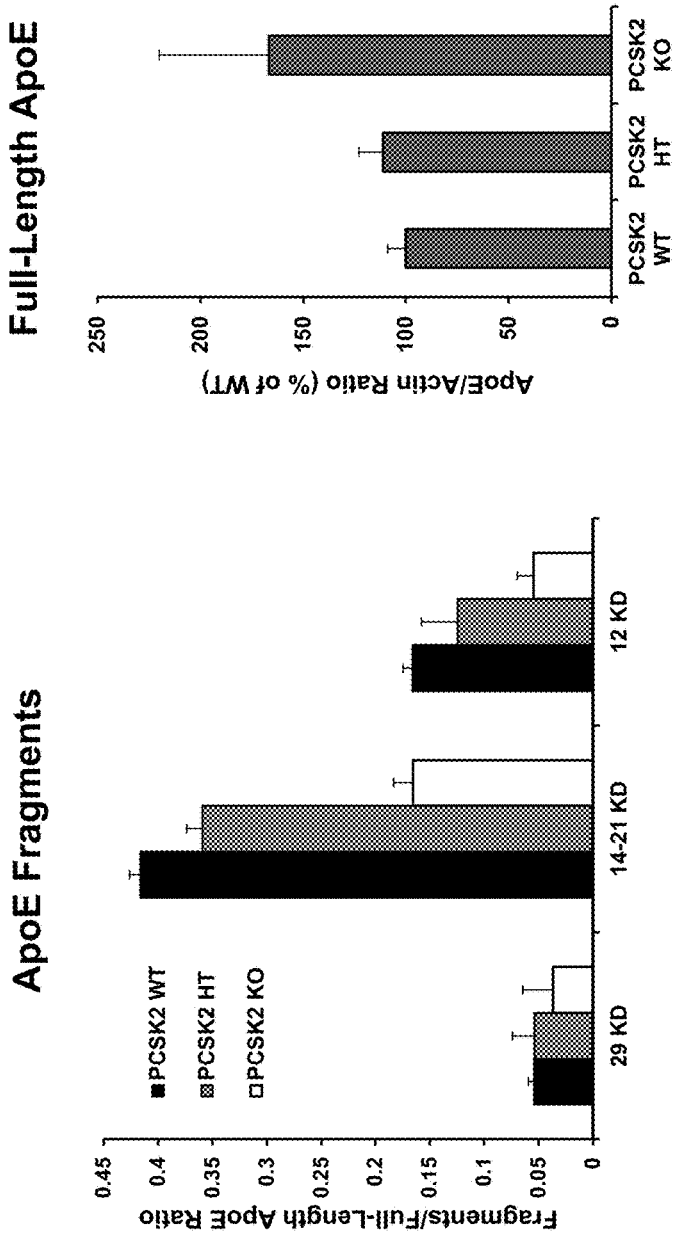

To determine whether PCSK2 contributes to neuronal apoE fragmentation in vivo, NSE-apoE4 mice were bred with a PCSK2 null mouse to obtain offspring expressing apoE4 in neurons with various PCSK2 genotypes (WT, HT, KO). Brains from adult mice were collected and apoE fragmentation was detected by western blot. As shown in FIG. 6, a significant decrease in apoE fragmentation was observed in PCSK2 null, NSE-apoE4 brains compared to that of PCSK2 WT, NSE-apoE4 brains. These results suggested that PCSK2 play a role in neuronal apoE fragmentation in vivo.

Additional study in primary neuron also supports a role for PCSK1/PCSK2 in neuronal apoE fragmentation. The effect of PCSK2 shRNAs and 7B2 (PCSK2 activator) shRNAs on PCSK1 null, NSE-apoE4 primary neurons was tested to determine whether PCSK1 and PCSK2 both contribute to neuronal apoE fragmentation. PCSK2 shRNAs or 7B2 shRNAs decrease apoE fragmentation in PCSK1 null, primary neurons as well as in PCSK1 WT primary neurons, suggesting that both PCSK1 and PCSK2 contribute to apoE fragmentation in primary neurons.

Example 2: PCSK1 Inhibitor Screen

An example of a suitable assay protocol for identifying PCSK1 inhibitors is as follows.

Assay buffer: 50 mM NaOAc, pH 6.0, 150 mM NaCl, 2 mM $CaCl_2$.

In a black bottom 96 well plate, 0.1 µg human PCSK1 (recombinant protein from R&D system) was mixed with various test compounds (1 µM final concentration) in 50 µl assay buffer for a half hour.

Figure 13:
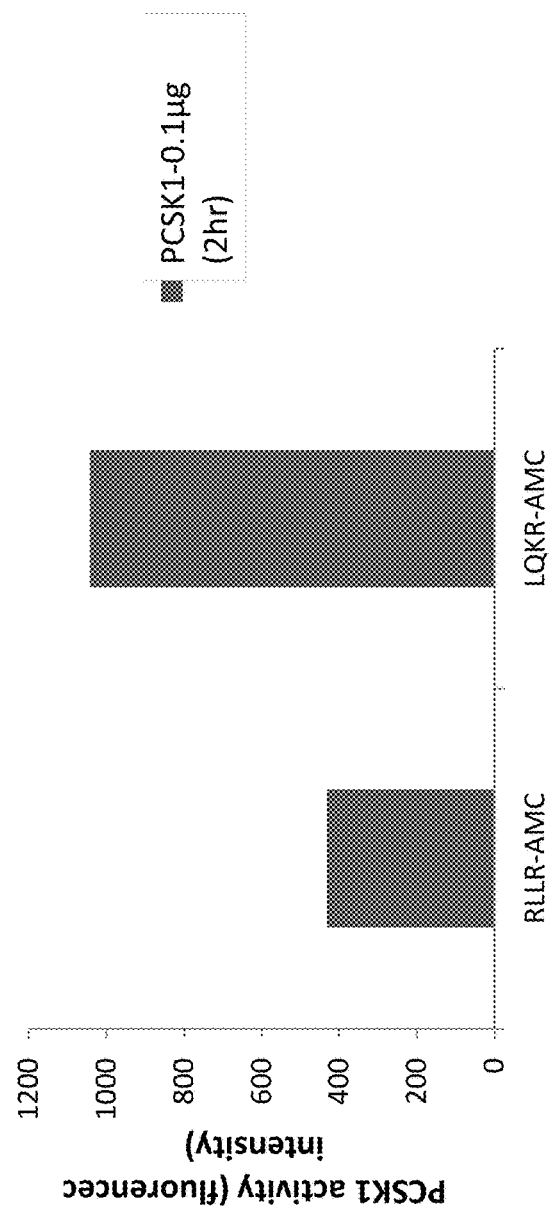
FIG. 13 depicts an in vitro assay of PCSK1 activity using an apoE-derived peptide as a substrate.

In the same plate, 0.1 µg human PCSK1 mixed with dimethylsulfoxide (DMSO) was used as positive control for activity (See, e.g., FIG. 13); 0.1 µg human PCSK1 with 5 mM EDTA in assay buffer was used as control for complete inhibition.

50 µl of RLLR-AMC or LQKR-AMC (100 µM in assay buffer), both of which are derived from apoE sequence, were added to the well to initiate the reaction. RLLR-AMC and LQKR-AMC are amc-labeled peptides, where amc is 7-amino-4-methlcoumarin.

The plate was sealed and covered with foil, and incubated 37° C. for 3 hr. Fluorescence was read with a plate reader (EX 380 nm/EM460 nm).

Example 3: PCSK2 Inhibitor Screen

An example of a suitable assay protocol for identifying PCSK2 inhibitors is as follows.

Assay buffer: 50 mM NaOAc, pH 6.0, 150 mM NaCl, 2 mM $CaCl_2$.

In a black bottom 96 well plate, 0.1 µg human PCSK2 (recombinant protein from R&D system) was mixed with various test compounds (1 µM final concentration) in 50 µl assay buffer for a half hour.

In the same plate, 0.1 µg human PCSK2 mixed with dimethylsulfoxide (DMSO) was used as positive control for activity (See, e.g., FIG. 14); 0.1 µg human PCSK2 with 5 mM EDTA in assay buffer was used as control for complete inhibition.

50 µl of LQKR-AMC (100 µM in assay buffer), which is derived from apoE sequence, were added to the well to initiate the reaction. LQKR-AMC is an amc-labeled peptide, where amc is 7-amino-4-methlcoumarin.

The plate was sealed and covered with foil, and incubated 37° C. for 3 hr. Fluorescence was read with a plate reader (EX 380 nm/EM460 nm).

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

What is claimed is:

1. A method for identifying a candidate agent for treating an apoE-associated neurodegenerative disorder, the method comprising
   a) contacting an isolated PCSK1 or an isolated PCSK2 polypeptide with an apoE polypeptide and a test agent; and
   b) determining the effect, if any, of the test agent on cleavage of the apoE polypeptide by the PCSK1 or PCSK2 polypeptide,
   wherein a test agent that reduces cleavage of the apoE polypeptide by the PCSK1 or PCSK2 polypeptide, compared to a control, is considered a candidate agent for treating an apoE-associated neurodegenerative disorder.

2. The method of claim 1, wherein the apoE polypeptide is an apoE4 polypeptide.

3. The method of claim 2, wherein the apoE4 polypeptide comprises an amino acid sequence having at least 75% amino acid sequence identity to the amino acid sequence depicted in FIG. 11A.

4. The method of claim 1, wherein the PCSK1 polypeptide comprises an amino acid sequence having at least 75% amino acid sequence identity to the amino acid sequence depicted in any one of FIGS. 7A, 7B, and 8.

5. The method of claim 1, wherein the PCSK2 polypeptide comprises an amino acid sequence having at least 75% amino acid sequence identity to the amino acid sequence depicted in any one of FIG. 9A, 9B, 9C, or 10.

6. The method of claim 2, wherein the apoE4 polypeptide comprises a fluorescent moiety.

7. An in vitro method for identifying a candidate agent for treating an apoE-associated neurodegenerative disorder, the method comprising
   a) contacting in a cell a PCSK1 or a PCSK2 polypeptide with an apoE polypeptide and a test agent; and
   b) determining the effect, if any, of the test agent on cleavage of the apoE polypeptide by the PCSK1 or PCSK2 polypeptide,
   wherein a test agent that reduces cleavage of the apoE polypeptide by the PCSK1 or PCSK2 polypeptide, compared to a control, is considered a candidate agent for treating an apoE-associated neurodegenerative disorder, and
   wherein the cell is genetically modified with:
      i) a nucleic acid comprising a nucleotide sequence encoding the PCSK1 polypeptide or the PCSK2 polypeptide; and
      ii) a nucleic acid comprising a nucleotide sequence encoding the apoE polypeptide.

8. The method of claim 7, wherein the nucleotide sequence encoding the PCSK1 polypeptide or the PCSK2 polypeptide is operably linked to a neuron-specific promoter.

9. The method of claim 7, wherein the nucleotide sequence encoding the apoE polypeptide is operably linked to a neuron-specific promoter.

10. The method of claim 1, wherein said determining comprises detecting apoE fragments.

11. The method of claim 6, wherein said determining comprises detecting a fluorescent signal.

12. The method of claim 6, wherein the fluorescent moiety is 7-amino-4-methyl-coumarin.

13. The method of claim 7, wherein the cell is a primary neuron or a neuronal cell line.

* * * * *

SEQUENCE LISTING

```
<160> NUMBER OF SEQ ID NOS: 15

<210> SEQ ID NO 1
<211> LENGTH: 753
<212> TYPE: PRT
<213> ORGANISM: Homo sapiens

<400> SEQUENCE: 1

Met Glu Arg Arg Ala Trp Ser Leu Gln Cys Thr Ala Phe Val Leu Phe
 1               5                  10                  15

Cys Ala Trp Cys Ala Leu Asn Ser Ala Lys Ala Lys Arg Gln Phe Val
                20                  25                  30

Asn Glu Trp Ala Ala Glu Ile Pro Gly Gly Pro Glu Ala Ala Ser Ala
            35                  40                  45

Ile Ala Glu Glu Leu Gly Tyr Asp Leu Leu Gly Gln Ile Gly Ser Leu
        50                  55                  60

Glu Asn His Tyr Leu Phe Lys His Lys Asn His Pro Arg Arg Ser Arg
65                  70                  75                  80

Arg Ser Ala Phe His Ile Thr Lys Arg Leu Ser Asp Asp Asp Arg Val
                85                  90                  95

Ile Trp Ala Glu Gln Gln Tyr Glu Lys Glu Arg Ser Lys Arg Ser Ala
            100                 105                 110

Leu Arg Asp Ser Ala Leu Asn Leu Phe Asn Asp Pro Met Trp Asn Gln
        115                 120                 125

Gln Trp Tyr Leu Gln Asp Thr Arg Met Thr Ala Ala Leu Pro Lys Leu
    130                 135                 140

Asp Leu His Val Ile Pro Val Trp Gln Lys Gly Ile Thr Gly Lys Gly
145                 150                 155                 160

Val Val Ile Thr Val Leu Asp Asp Gly Leu Glu Trp Asn His Thr Asp
                165                 170                 175

Ile Tyr Ala Asn Tyr Asp Pro Glu Ala Ser Tyr Asp Phe Asn Asp Asn
            180                 185                 190

Asp His Asp Pro Phe Pro Arg Tyr Asp Pro Thr Asn Glu Asn Lys His
        195                 200                 205

Gly Thr Arg Cys Ala Gly Glu Ile Ala Met Gln Ala Asn Asn His Lys
    210                 215                 220

Cys Gly Val Gly Val Ala Tyr Asn Ser Lys Val Gly Gly Ile Arg Met
225                 230                 235                 240

Leu Asp Gly Ile Val Thr Asp Ala Ile Glu Ala Ser Ser Ile Gly Phe
                245                 250                 255

Asn Pro Gly His Val Asp Ile Tyr Ser Ala Ser Trp Gly Pro Asn Asp
            260                 265                 270

Asp Gly Lys Thr Val Glu Gly Pro Gly Arg Leu Ala Gln Lys Ala Phe
        275                 280                 285

Glu Tyr Gly Val Lys Gln Gly Arg Gln Gly Lys Gly Ser Ile Phe Val
    290                 295                 300
```

-continued

```
Trp Ala Ser Gly Asn Gly Gly Arg Gln Gly Asp Asn Cys Asp Cys Asp
305                 310                 315                 320

Gly Tyr Thr Asp Ser Ile Tyr Thr Ile Ser Ile Ser Ser Ala Ser Gln
                325                 330                 335

Gln Gly Leu Ser Pro Trp Tyr Ala Glu Lys Cys Ser Ser Thr Leu Ala
            340                 345                 350

Thr Ser Tyr Ser Ser Gly Asp Tyr Thr Asp Gln Arg Ile Thr Ser Ala
        355                 360                 365

Asp Leu His Asn Asp Cys Thr Glu Thr His Thr Gly Thr Ser Ala Ser
    370                 375                 380

Ala Pro Leu Ala Ala Gly Ile Phe Ala Leu Ala Leu Glu Ala Asn Pro
385                 390                 395                 400

Asn Leu Thr Trp Arg Asp Met Gln His Leu Val Val Trp Thr Ser Glu
                405                 410                 415

Tyr Asp Pro Leu Ala Asn Asn Pro Gly Trp Lys Lys Asn Gly Ala Gly
                420                 425                 430

Leu Met Val Asn Ser Arg Phe Gly Phe Gly Leu Leu Asn Ala Lys Ala
            435                 440                 445

Leu Val Asp Leu Ala Asp Pro Arg Thr Trp Arg Ser Val Pro Glu Lys
    450                 455                 460

Lys Glu Cys Val Val Lys Asp Asn Asp Phe Glu Pro Arg Ala Leu Lys
465                 470                 475                 480

Ala Asn Gly Glu Val Ile Ile Glu Ile Pro Thr Arg Ala Cys Glu Gly
                485                 490                 495

Gln Glu Asn Ala Ile Lys Ser Leu Glu His Val Gln Phe Glu Ala Thr
            500                 505                 510

Ile Glu Tyr Ser Arg Arg Gly Asp Leu His Val Thr Leu Thr Ser Ala
        515                 520                 525

Ala Gly Thr Ser Thr Val Leu Leu Ala Glu Arg Glu Arg Asp Thr Ser
    530                 535                 540

Pro Asn Gly Phe Lys Asn Trp Asp Phe Met Ser Val His Thr Trp Gly
545                 550                 555                 560

Glu Asn Pro Ile Gly Thr Trp Thr Leu Arg Ile Thr Asp Met Ser Gly
                565                 570                 575

Arg Ile Gln Asn Glu Gly Arg Ile Val Asn Trp Lys Leu Ile Leu His
                580                 585                 590

Gly Thr Ser Ser Gln Pro Glu His Met Lys Gln Pro Arg Val Tyr Thr
            595                 600                 605

Ser Tyr Asn Thr Val Gln Asn Asp Arg Arg Gly Val Glu Lys Met Val
        610                 615                 620

Asp Pro Gly Glu Glu Gln Pro Thr Gln Glu Asn Pro Lys Glu Asn Thr
625                 630                 635                 640

Leu Val Ser Lys Ser Pro Ser Ser Ser Val Gly Gly Arg Arg Asp
                645                 650                 655

Glu Leu Glu Glu Gly Ala Pro Ser Gln Ala Met Leu Arg Leu Leu Gln
            660                 665                 670

Ser Ala Phe Ser Lys Asn Ser Pro Pro Lys Gln Ser Pro Lys Lys Ser
        675                 680                 685

Pro Ser Ala Lys Leu Asn Ile Pro Tyr Glu Asn Phe Tyr Glu Ala Leu
    690                 695                 700

Glu Lys Leu Asn Lys Pro Ser Gln Leu Lys Asp Ser Glu Asp Ser Leu
705                 710                 715                 720
```

-continued

Tyr Asn Asp Tyr Val Asp Val Phe Tyr Asn Thr Lys Pro Tyr Lys His
                    725                 730                 735

Arg Asp Asp Arg Leu Leu Gln Ala Leu Val Asp Ile Leu Asn Glu Glu
            740                 745                 750

Asn

<210> SEQ ID NO 2
<211> LENGTH: 59
<212> TYPE: PRT
<213> ORGANISM: Homo sapiens

<400> SEQUENCE: 2

Met Glu Arg Arg Ala Trp Ser Leu Gln Cys Thr Ala Phe Val Leu Phe
1               5                   10                  15

Cys Ala Trp Cys Ala Leu Asn Ser Ala Lys Ala Lys Arg Gln Phe Val
                20                  25                  30

Asn Glu Trp Ala Ala Glu Ile Pro Gly Gly Pro Glu Ala Ala Ser Ala
            35                  40                  45

Ile Ala Glu Glu Leu Gly Tyr Asp Leu Leu Gly
        50                  55

<210> SEQ ID NO 3
<211> LENGTH: 12
<212> TYPE: PRT
<213> ORGANISM: Homo sapiens

<400> SEQUENCE: 3

Met Gly Lys Gly Ser Ile Ser Phe Leu Phe Phe Ser
1               5                   10

<210> SEQ ID NO 4
<211> LENGTH: 706
<212> TYPE: PRT
<213> ORGANISM: Homo sapiens

<400> SEQUENCE: 4

Met Gly Lys Gly Ser Ile Ser Phe Leu Phe Phe Ser Gln Ile Gly Ser
1               5                   10                  15

Leu Glu Asn His Tyr Leu Phe Lys His Lys Asn His Pro Arg Arg Ser
                20                  25                  30

Arg Arg Ser Ala Phe His Ile Thr Lys Arg Leu Ser Asp Asp Arg
            35                  40                  45

Val Ile Trp Ala Glu Gln Gln Tyr Glu Lys Glu Arg Ser Lys Arg Ser
        50                  55                  60

Ala Leu Arg Asp Ser Ala Leu Asn Leu Phe Asn Asp Pro Met Trp Asn
65                  70                  75                  80

Gln Gln Trp Tyr Leu Gln Asp Thr Arg Met Thr Ala Ala Leu Pro Lys
                85                  90                  95

Leu Asp Leu His Val Ile Pro Val Trp Gln Lys Gly Ile Thr Gly Lys
            100                 105                 110

Gly Val Val Ile Thr Val Leu Asp Asp Gly Leu Glu Trp Asn His Thr
        115                 120                 125

Asp Ile Tyr Ala Asn Tyr Asp Pro Glu Ala Ser Tyr Asp Phe Asn Asp
    130                 135                 140

Asn Asp His Asp Pro Phe Pro Arg Tyr Asp Pro Thr Asn Glu Asn Lys
145                 150                 155                 160

His Gly Thr Arg Cys Ala Gly Glu Ile Ala Met Gln Ala Asn Asn His
                165                 170                 175

-continued

```
Lys Cys Gly Val Gly Val Ala Tyr Asn Ser Lys Val Gly Ile Arg
            180                 185                 190
Met Leu Asp Gly Ile Val Thr Asp Ala Ile Glu Ala Ser Ile Gly
            195                 200                 205
Phe Asn Pro Gly His Val Asp Ile Tyr Ser Ala Ser Trp Gly Pro Asn
            210                 215                 220
Asp Asp Gly Lys Thr Val Glu Gly Pro Gly Arg Leu Ala Gln Lys Ala
225                 230                 235                 240
Phe Glu Tyr Gly Val Lys Gln Gly Arg Gln Gly Lys Gly Ser Ile Phe
                245                 250                 255
Val Trp Ala Ser Gly Asn Gly Gly Arg Gln Gly Asp Asn Cys Asp Cys
            260                 265                 270
Asp Gly Tyr Thr Asp Ser Ile Tyr Thr Ile Ser Ile Ser Ser Ala Ser
            275                 280                 285
Gln Gln Gly Leu Ser Pro Trp Tyr Ala Glu Lys Cys Ser Ser Thr Leu
            290                 295                 300
Ala Thr Ser Tyr Ser Ser Gly Asp Tyr Thr Asp Gln Arg Ile Thr Ser
305                 310                 315                 320
Ala Asp Leu His Asn Asp Cys Thr Glu Thr His Thr Gly Thr Ser Ala
                325                 330                 335
Ser Ala Pro Leu Ala Ala Gly Ile Phe Ala Leu Ala Leu Glu Ala Asn
            340                 345                 350
Pro Asn Leu Thr Trp Arg Asp Met Gln His Leu Val Val Trp Thr Ser
            355                 360                 365
Glu Tyr Asp Pro Leu Ala Asn Asn Pro Gly Trp Lys Lys Asn Gly Ala
            370                 375                 380
Gly Leu Met Val Asn Ser Arg Phe Gly Phe Gly Leu Leu Asn Ala Lys
385                 390                 395                 400
Ala Leu Val Asp Leu Ala Asp Pro Arg Thr Trp Arg Ser Val Pro Glu
                405                 410                 415
Lys Lys Glu Cys Val Val Lys Asp Asn Asp Phe Glu Pro Arg Ala Leu
            420                 425                 430
Lys Ala Asn Gly Glu Val Ile Ile Glu Ile Pro Thr Arg Ala Cys Glu
            435                 440                 445
Gly Gln Glu Asn Ala Ile Lys Ser Leu Glu His Val Gln Phe Glu Ala
            450                 455                 460
Thr Ile Glu Tyr Ser Arg Arg Gly Asp Leu His Val Thr Leu Thr Ser
465                 470                 475                 480
Ala Ala Gly Thr Ser Thr Val Leu Leu Ala Glu Arg Glu Arg Asp Thr
                485                 490                 495
Ser Pro Asn Gly Phe Lys Asn Trp Asp Phe Met Ser Val His Thr Trp
            500                 505                 510
Gly Glu Asn Pro Ile Gly Thr Trp Thr Leu Arg Ile Thr Asp Met Ser
            515                 520                 525
Gly Arg Ile Gln Asn Glu Gly Arg Ile Val Asn Trp Lys Leu Ile Leu
            530                 535                 540
His Gly Thr Ser Ser Gln Pro Glu His Met Lys Gln Pro Arg Val Tyr
545                 550                 555                 560
Thr Ser Tyr Asn Thr Val Gln Asn Asp Arg Arg Gly Val Glu Lys Met
                565                 570                 575
Val Asp Pro Gly Glu Glu Gln Pro Thr Gln Glu Asn Pro Lys Glu Asn
            580                 585                 590
```

```
Thr Leu Val Ser Lys Ser Pro Ser Ser Ser Val Gly Gly Arg Arg
            595                 600                 605

Asp Glu Leu Glu Glu Gly Ala Pro Ser Gln Ala Met Leu Arg Leu Leu
610                 615                 620

Gln Ser Ala Phe Ser Lys Asn Ser Pro Pro Lys Gln Ser Pro Lys Lys
625                 630                 635                 640

Ser Pro Ser Ala Lys Leu Asn Ile Pro Tyr Glu Asn Phe Tyr Glu Ala
                645                 650                 655

Leu Glu Lys Leu Asn Lys Pro Ser Gln Leu Lys Asp Ser Glu Asp Ser
                660                 665                 670

Leu Tyr Asn Asp Tyr Val Asp Val Phe Tyr Asn Thr Lys Pro Tyr Lys
                675                 680                 685

His Arg Asp Asp Arg Leu Leu Gln Ala Leu Val Asp Ile Leu Asn Glu
            690                 695                 700

Glu Asn
705

<210> SEQ ID NO 5
<211> LENGTH: 753
<212> TYPE: PRT
<213> ORGANISM: Mus musculus

<400> SEQUENCE: 5

Met Glu Gln Arg Gly Trp Thr Leu Gln Cys Thr Ala Phe Ala Phe Phe
1               5                   10                  15

Cys Val Trp Cys Ala Leu Asn Ser Val Lys Ala Lys Arg Gln Phe Val
                20                  25                  30

Asn Glu Trp Ala Ala Glu Ile Pro Gly Gly Gln Glu Ala Ala Ser Ala
            35                  40                  45

Ile Ala Glu Glu Leu Gly Tyr Asp Leu Leu Gly Gln Ile Gly Ser Leu
    50                  55                  60

Glu Asn His Tyr Leu Phe Lys His Lys Ser His Pro Arg Arg Ser Arg
65              70                  75                  80

Arg Ser Ala Leu His Ile Thr Lys Arg Leu Ser Asp Asp Asp Arg Val
                85                  90                  95

Thr Trp Ala Glu Gln Gln Tyr Glu Lys Glu Arg Ser Lys Arg Ser Val
            100                 105                 110

Gln Lys Asp Ser Ala Leu Asp Leu Phe Asn Asp Pro Met Trp Asn Gln
        115                 120                 125

Gln Trp Tyr Leu Gln Asp Thr Arg Met Thr Ala Ala Leu Pro Lys Leu
    130                 135                 140

Asp Leu His Val Ile Pro Val Trp Glu Lys Gly Ile Thr Gly Lys Gly
145                 150                 155                 160

Val Val Ile Thr Val Leu Asp Asp Gly Leu Glu Trp Asn His Thr Asp
                165                 170                 175

Ile Tyr Ala Asn Tyr Asp Pro Glu Ala Ser Tyr Asp Phe Asn Asp Asn
            180                 185                 190

Asp His Asp Pro Phe Pro Arg Tyr Asp Leu Thr Asn Glu Asn Lys His
        195                 200                 205

Gly Thr Arg Cys Ala Gly Glu Ile Ala Met Gln Ala Asn Asn His Lys
    210                 215                 220

Cys Gly Val Gly Val Ala Tyr Asn Ser Lys Val Gly Gly Ile Arg Met
225                 230                 235                 240

Leu Asp Gly Ile Val Thr Asp Ala Ile Glu Ala Ser Ser Ile Gly Phe
                245                 250                 255
```

```
Asn Pro Gly His Val Asp Ile Tyr Ser Ala Ser Trp Gly Pro Asn Asp
            260                 265                 270

Asp Gly Lys Thr Val Glu Gly Pro Gly Arg Leu Ala Gln Lys Ala Phe
            275                 280                 285

Glu Tyr Gly Val Lys Gln Gly Arg Gln Gly Lys Gly Ser Ile Phe Val
            290                 295                 300

Trp Ala Ser Gly Asn Gly Gly Arg Gln Gly Asp Asn Cys Asp Cys Asp
305                 310                 315                 320

Gly Tyr Thr Asp Ser Ile Tyr Thr Ile Ser Ile Ser Ser Ala Ser Gln
            325                 330                 335

Gln Gly Leu Ser Pro Trp Tyr Ala Glu Lys Cys Ser Ser Thr Leu Ala
            340                 345                 350

Thr Ser Tyr Ser Ser Gly Asp Tyr Thr Asp Gln Arg Ile Thr Ser Ala
            355                 360                 365

Asp Leu His Asn Asp Cys Thr Glu Thr His Thr Gly Thr Ser Ala Ser
            370                 375                 380

Ala Pro Leu Ala Ala Gly Ile Phe Ala Leu Ala Leu Glu Ala Asn Pro
385                 390                 395                 400

Asn Leu Thr Trp Arg Asp Met Gln His Leu Val Val Trp Thr Ser Glu
            405                 410                 415

Tyr Asp Pro Leu Ala Ser Asn Pro Gly Trp Lys Lys Asn Gly Ala Gly
            420                 425                 430

Leu Met Val Asn Ser Arg Phe Gly Phe Gly Leu Leu Asn Ala Lys Ala
            435                 440                 445

Leu Val Asp Leu Ala Asp Pro Arg Thr Trp Arg Asn Val Pro Glu Lys
            450                 455                 460

Lys Glu Cys Val Val Lys Asp Asn Asn Phe Glu Pro Arg Ala Leu Lys
465                 470                 475                 480

Ala Asn Gly Glu Val Ile Val Glu Ile Pro Thr Arg Ala Cys Glu Gly
            485                 490                 495

Gln Glu Asn Ala Ile Lys Ser Leu Glu His Val Gln Phe Glu Ala Thr
            500                 505                 510

Ile Glu Tyr Ser Arg Arg Gly Asp Leu His Val Thr Leu Thr Ser Ala
            515                 520                 525

Val Gly Thr Ser Thr Val Leu Leu Ala Glu Arg Glu Arg Asp Thr Ser
            530                 535                 540

Pro Asn Gly Phe Lys Asn Trp Asp Phe Met Ser Val His Thr Trp Gly
545                 550                 555                 560

Glu Asn Pro Val Gly Thr Trp Thr Leu Lys Ile Thr Asp Met Ser Gly
            565                 570                 575

Arg Met Gln Asn Glu Gly Arg Ile Val Asn Trp Lys Leu Ile Leu His
            580                 585                 590

Gly Thr Ser Ser Gln Pro Glu His Met Lys Gln Pro Arg Val Tyr Thr
            595                 600                 605

Ser Tyr Asn Thr Val Gln Asn Asp Arg Arg Gly Val Glu Lys Met Val
            610                 615                 620

Asn Val Val Glu Lys Arg Pro Thr Gln Lys Ser Leu Asn Gly Asn Leu
625                 630                 635                 640

Leu Val Pro Lys Asn Ser Ser Ser Asn Val Glu Gly Arg Arg Asp
            645                 650                 655

Glu Gln Val Gln Gly Thr Pro Ser Lys Ala Met Leu Arg Leu Leu Gln
            660                 665                 670
```

```
Ser Ala Phe Ser Lys Asn Ala Leu Ser Lys Gln Ser Pro Lys Lys Ser
            675                 680                 685

Pro Ser Ala Lys Leu Ser Ile Pro Tyr Glu Ser Phe Tyr Glu Ala Leu
690                 695                 700

Glu Lys Leu Asn Lys Pro Ser Lys Leu Glu Gly Ser Glu Asp Ser Leu
705                 710                 715                 720

Tyr Ser Asp Tyr Val Asp Val Phe Tyr Asn Thr Lys Pro Tyr Lys His
                725                 730                 735

Arg Asp Asp Arg Leu Leu Gln Ala Leu Met Asp Ile Leu Asn Glu Glu
                740                 745                 750

Asn

<210> SEQ ID NO 6
<211> LENGTH: 638
<212> TYPE: PRT
<213> ORGANISM: Homo sapiens

<400> SEQUENCE: 6

Met Lys Gly Gly Cys Val Ser Gln Trp Lys Ala Ala Gly Phe Leu
 1               5                  10                  15

Phe Cys Val Met Val Phe Ala Ser Ala Glu Arg Pro Val Phe Thr Asn
                20                  25                  30

His Phe Leu Val Glu Leu His Lys Gly Gly Glu Asp Lys Ala Arg Gln
            35                  40                  45

Val Ala Ala Glu His Gly Phe Gly Val Arg Lys Leu Pro Phe Ala Glu
        50                  55                  60

Gly Leu Tyr His Phe Tyr His Asn Gly Leu Ala Lys Ala Lys Arg Arg
65                  70                  75                  80

Arg Ser Leu His His Lys Gln Gln Leu Glu Arg Asp Pro Arg Val Lys
                85                  90                  95

Met Ala Leu Gln Gln Glu Gly Phe Asp Arg Lys Lys Arg Gly Tyr Arg
            100                 105                 110

Asp Ile Asn Glu Ile Asp Ile Asn Met Asn Asp Pro Leu Phe Thr Lys
        115                 120                 125

Gln Trp Tyr Leu Ile Asn Thr Gly Gln Ala Asp Gly Thr Pro Gly Leu
    130                 135                 140

Asp Leu Asn Val Ala Glu Ala Trp Glu Leu Gly Tyr Thr Gly Lys Gly
145                 150                 155                 160

Val Thr Ile Gly Ile Met Asp Asp Gly Ile Asp Tyr Leu His Pro Asp
                165                 170                 175

Leu Ala Ser Asn Tyr Asn Ala Glu Ala Ser Tyr Asp Phe Ser Ser Asn
            180                 185                 190

Asp Pro Tyr Pro Tyr Pro Arg Tyr Thr Asp Asp Trp Phe Asn Ser His
        195                 200                 205

Gly Thr Arg Cys Ala Gly Glu Val Ser Ala Ala Ala Asn Asn Asn Ile
    210                 215                 220

Cys Gly Val Gly Val Ala Tyr Asn Ser Lys Val Ala Gly Ile Arg Met
225                 230                 235                 240

Leu Asp Gln Pro Phe Met Thr Asp Ile Ile Glu Ala Ser Ser Ile Ser
                245                 250                 255

His Met Pro Gln Leu Ile Asp Ile Tyr Ser Ala Ser Trp Gly Pro Thr
            260                 265                 270

Asp Asn Gly Lys Thr Val Asp Gly Pro Arg Glu Leu Thr Leu Gln Ala
        275                 280                 285
```

```
Met Ala Asp Gly Val Asn Lys Gly Arg Gly Gly Lys Gly Ser Ile Tyr
    290                 295                 300

Val Trp Ala Ser Gly Asp Gly Ser Tyr Asp Asp Cys Asn Cys Asp
305                 310                 315                 320

Gly Tyr Ala Ser Ser Met Trp Thr Ile Ser Ile Asn Ser Ala Ile Asn
                    325                 330                 335

Asp Gly Arg Thr Ala Leu Tyr Asp Glu Ser Cys Ser Ser Thr Leu Ala
                340                 345                 350

Ser Thr Phe Ser Asn Gly Arg Lys Arg Asn Pro Glu Ala Gly Val Ala
                355                 360                 365

Thr Thr Asp Leu Tyr Gly Asn Cys Thr Leu Arg His Ser Gly Thr Ser
370                 375                 380

Ala Ala Ala Pro Glu Ala Ala Gly Val Phe Ala Leu Ala Leu Glu Ala
385                 390                 395                 400

Asn Leu Gly Leu Thr Trp Arg Asp Met Gln His Leu Thr Val Leu Thr
                    405                 410                 415

Ser Lys Arg Asn Gln Leu His Asp Glu Val His Gln Trp Arg Arg Asn
                420                 425                 430

Gly Val Gly Leu Glu Phe Asn His Leu Phe Gly Tyr Gly Val Leu Asp
                435                 440                 445

Ala Gly Ala Met Val Lys Met Ala Lys Asp Trp Lys Thr Val Pro Glu
450                 455                 460

Arg Phe His Cys Val Gly Ser Val Gln Asp Pro Glu Lys Ile Pro
465                 470                 475                 480

Ser Thr Gly Lys Leu Val Leu Thr Leu Thr Thr Asp Ala Cys Glu Gly
                    485                 490                 495

Lys Glu Asn Phe Val Arg Tyr Leu Glu His Val Gln Ala Val Ile Thr
                500                 505                 510

Val Asn Ala Thr Arg Arg Gly Asp Leu Asn Ile Asn Met Thr Ser Pro
            515                 520                 525

Met Gly Thr Lys Ser Ile Leu Leu Ser Arg Arg Pro Arg Asp Asp Asp
    530                 535                 540

Ser Lys Val Gly Phe Asp Lys Trp Pro Phe Met Thr Thr His Thr Trp
545                 550                 555                 560

Gly Glu Asp Ala Arg Gly Thr Trp Thr Leu Glu Leu Gly Phe Val Gly
                565                 570                 575

Ser Ala Pro Gln Lys Gly Val Leu Lys Glu Trp Thr Leu Met Leu His
                580                 585                 590

Gly Thr Gln Ser Ala Pro Tyr Ile Asp Gln Val Val Arg Asp Tyr Gln
                595                 600                 605

Ser Lys Leu Ala Met Ser Lys Lys Glu Glu Leu Glu Glu Glu Leu Asp
                610                 615                 620

Glu Ala Val Glu Arg Ser Leu Lys Ser Ile Leu Asn Lys Asn
625                 630                 635

<210> SEQ ID NO 7
<211> LENGTH: 603
<212> TYPE: PRT
<213> ORGANISM: Homo sapiens

<400> SEQUENCE: 7

Met Lys Gly Gly Cys Val Ser Gln Trp Lys Ala Ala Gly Phe Leu
1               5                   10                  15

Phe Cys Val Met Val Phe Ala Ser Ala Glu Arg Pro Val Phe Thr Asn
                20                  25                  30
```

```
His Phe Leu Val Glu Leu His Lys Gly Gly Glu Asp Lys Ala Arg Gln
         35                  40                  45

Val Ala Ala Glu His Gly Phe Gly Val Arg Lys Val Lys Met Ala Leu
 50                  55                  60

Gln Gln Glu Gly Phe Asp Arg Lys Lys Arg Gly Tyr Arg Asp Ile Asn
 65                  70                  75                  80

Glu Ile Asp Ile Asn Met Asn Asp Pro Leu Phe Thr Lys Gln Trp Tyr
                 85                  90                  95

Leu Ile Asn Thr Gly Gln Ala Asp Gly Thr Pro Gly Leu Asp Leu Asn
                100                 105                 110

Val Ala Glu Ala Trp Glu Leu Gly Tyr Thr Gly Lys Gly Val Thr Ile
            115                 120                 125

Gly Ile Met Asp Asp Gly Ile Asp Tyr Leu His Pro Asp Leu Ala Ser
        130                 135                 140

Asn Tyr Asn Ala Glu Ala Ser Tyr Asp Phe Ser Ser Asn Asp Pro Tyr
145                 150                 155                 160

Pro Tyr Pro Arg Tyr Thr Asp Asp Trp Phe Asn Ser His Gly Thr Arg
                165                 170                 175

Cys Ala Gly Glu Val Ser Ala Ala Ala Asn Asn Asn Ile Cys Gly Val
                180                 185                 190

Gly Val Ala Tyr Asn Ser Lys Val Ala Gly Ile Arg Met Leu Asp Gln
            195                 200                 205

Pro Phe Met Thr Asp Ile Ile Glu Ala Ser Ser Ile Ser His Met Pro
        210                 215                 220

Gln Leu Ile Asp Ile Tyr Ser Ala Ser Trp Gly Pro Thr Asp Asn Gly
225                 230                 235                 240

Lys Thr Val Asp Gly Pro Arg Glu Leu Thr Leu Gln Ala Met Ala Asp
                245                 250                 255

Gly Val Asn Lys Gly Arg Gly Gly Lys Gly Ser Ile Tyr Val Trp Ala
                260                 265                 270

Ser Gly Asp Gly Gly Ser Tyr Asp Asp Cys Asn Cys Asp Gly Tyr Ala
            275                 280                 285

Ser Ser Met Trp Thr Ile Ser Ile Asn Ser Ala Ile Asn Asp Gly Arg
        290                 295                 300

Thr Ala Leu Tyr Asp Glu Ser Cys Ser Ser Thr Leu Ala Ser Thr Phe
305                 310                 315                 320

Ser Asn Gly Arg Lys Arg Asn Pro Glu Ala Gly Val Ala Thr Thr Asp
                325                 330                 335

Leu Tyr Gly Asn Cys Thr Leu Arg His Ser Gly Thr Ser Ala Ala Ala
                340                 345                 350

Pro Glu Ala Ala Gly Val Phe Ala Leu Ala Leu Glu Ala Asn Leu Gly
            355                 360                 365

Leu Thr Trp Arg Asp Met Gln His Leu Thr Val Leu Thr Ser Lys Arg
        370                 375                 380

Asn Gln Leu His Asp Glu Val His Gln Trp Arg Arg Asn Gly Val Gly
385                 390                 395                 400

Leu Glu Phe Asn His Leu Phe Gly Tyr Gly Val Leu Asp Ala Gly Ala
                405                 410                 415

Met Val Lys Met Ala Lys Asp Trp Lys Thr Val Pro Glu Arg Phe His
                420                 425                 430

Cys Val Gly Gly Ser Val Gln Asp Pro Glu Lys Ile Pro Ser Thr Gly
            435                 440                 445
```

```
Lys Leu Val Leu Thr Leu Thr Thr Asp Ala Cys Glu Gly Lys Glu Asn
450                 455                 460

Phe Val Arg Tyr Leu Glu His Val Gln Ala Val Ile Thr Val Asn Ala
465                 470                 475                 480

Thr Arg Arg Gly Asp Leu Asn Ile Asn Met Thr Ser Pro Met Gly Thr
                485                 490                 495

Lys Ser Ile Leu Leu Ser Arg Arg Pro Arg Asp Asp Ser Lys Val
                500                 505                 510

Gly Phe Asp Lys Trp Pro Phe Met Thr Thr His Thr Trp Gly Glu Asp
                515                 520                 525

Ala Arg Gly Thr Trp Thr Leu Glu Leu Gly Phe Val Gly Ser Ala Pro
530                 535                 540

Gln Lys Gly Val Leu Lys Glu Trp Thr Leu Met Leu His Gly Thr Gln
545                 550                 555                 560

Ser Ala Pro Tyr Ile Asp Gln Val Val Arg Asp Tyr Gln Ser Lys Leu
                565                 570                 575

Ala Met Ser Lys Lys Glu Glu Leu Glu Glu Leu Asp Glu Ala Val
                580                 585                 590

Glu Arg Ser Leu Lys Ser Ile Leu Asn Lys Asn
                595                 600

<210> SEQ ID NO 8
<211> LENGTH: 619
<212> TYPE: PRT
<213> ORGANISM: Homo sapiens

<400> SEQUENCE: 8

Met Val Phe Ala Ser Ala Glu Arg Pro Val Phe Thr Asn His Phe Leu
1               5                   10                  15

Val Glu Leu His Lys Gly Gly Glu Asp Lys Ala Arg Gln Val Ala Ala
                20                  25                  30

Glu His Gly Phe Gly Val Arg Lys Leu Pro Phe Ala Glu Gly Leu Tyr
            35                  40                  45

His Phe Tyr His Asn Gly Leu Ala Lys Ala Lys Arg Arg Arg Ser Leu
        50                  55                  60

His His Lys Gln Gln Leu Glu Arg Asp Pro Arg Val Lys Met Ala Leu
65                  70                  75                  80

Gln Gln Glu Gly Phe Asp Arg Lys Lys Arg Gly Tyr Arg Asp Ile Asn
                85                  90                  95

Glu Ile Asp Ile Asn Met Asn Asp Pro Leu Phe Thr Lys Gln Trp Tyr
            100                 105                 110

Leu Ile Asn Thr Gly Gln Ala Asp Gly Thr Pro Gly Leu Asp Leu Asn
        115                 120                 125

Val Ala Glu Ala Trp Glu Leu Gly Tyr Thr Gly Lys Gly Val Thr Ile
130                 135                 140

Gly Ile Met Asp Asp Gly Ile Asp Tyr Leu His Pro Asp Leu Ala Ser
145                 150                 155                 160

Asn Tyr Asn Ala Glu Ala Ser Tyr Asp Phe Ser Ser Asn Asp Pro Tyr
                165                 170                 175

Pro Tyr Pro Arg Tyr Thr Asp Asp Trp Phe Asn Ser His Gly Thr Arg
            180                 185                 190

Cys Ala Gly Glu Val Ser Ala Ala Asn Asn Asn Ile Cys Gly Val
        195                 200                 205

Gly Val Ala Tyr Asn Ser Lys Val Ala Gly Ile Arg Met Leu Asp Gln
210                 215                 220
```

-continued

```
Pro Phe Met Thr Asp Ile Ile Glu Ala Ser Ser Ile Ser His Met Pro
225                 230                 235                 240

Gln Leu Ile Asp Ile Tyr Ser Ala Ser Trp Gly Pro Thr Asp Asn Gly
            245                 250                 255

Lys Thr Val Asp Gly Pro Arg Glu Leu Thr Leu Gln Ala Met Ala Asp
        260                 265                 270

Gly Val Asn Lys Gly Arg Gly Gly Lys Gly Ser Ile Tyr Val Trp Ala
    275                 280                 285

Ser Gly Asp Gly Gly Ser Tyr Asp Asp Cys Asn Cys Asp Gly Tyr Ala
290                 295                 300

Ser Ser Met Trp Thr Ile Ser Ile Asn Ser Ala Ile Asn Asp Gly Arg
305                 310                 315                 320

Thr Ala Leu Tyr Asp Glu Ser Cys Ser Ser Thr Leu Ala Ser Thr Phe
                325                 330                 335

Ser Asn Gly Arg Lys Arg Asn Pro Glu Ala Gly Val Ala Thr Thr Asp
            340                 345                 350

Leu Tyr Gly Asn Cys Thr Leu Arg His Ser Gly Thr Ser Ala Ala Ala
        355                 360                 365

Pro Glu Ala Ala Gly Val Phe Ala Leu Ala Leu Glu Ala Asn Leu Gly
    370                 375                 380

Leu Thr Trp Arg Asp Met Gln His Leu Thr Val Leu Thr Ser Lys Arg
385                 390                 395                 400

Asn Gln Leu His Asp Glu Val His Gln Trp Arg Arg Asn Gly Val Gly
                405                 410                 415

Leu Glu Phe Asn His Leu Phe Gly Tyr Gly Val Leu Asp Ala Gly Ala
            420                 425                 430

Met Val Lys Met Ala Lys Asp Trp Lys Thr Val Pro Glu Arg Phe His
        435                 440                 445

Cys Val Gly Gly Ser Val Gln Asp Pro Glu Lys Ile Pro Ser Thr Gly
    450                 455                 460

Lys Leu Val Leu Thr Leu Thr Thr Asp Ala Cys Glu Gly Lys Glu Asn
465                 470                 475                 480

Phe Val Arg Tyr Leu Glu His Val Gln Ala Val Ile Thr Val Asn Ala
                485                 490                 495

Thr Arg Arg Gly Asp Leu Asn Ile Asn Met Thr Ser Pro Met Gly Thr
            500                 505                 510

Lys Ser Ile Leu Leu Ser Arg Arg Pro Arg Asp Asp Ser Lys Val
        515                 520                 525

Gly Phe Asp Lys Trp Pro Phe Met Thr Thr His Thr Trp Gly Glu Asp
    530                 535                 540

Ala Arg Gly Thr Trp Thr Leu Glu Leu Gly Phe Val Gly Ser Ala Pro
545                 550                 555                 560

Gln Lys Gly Val Leu Lys Glu Trp Thr Leu Met Leu His Gly Thr Gln
                565                 570                 575

Ser Ala Pro Tyr Ile Asp Gln Val Val Arg Asp Tyr Gln Ser Lys Leu
            580                 585                 590

Ala Met Ser Lys Lys Glu Glu Leu Glu Glu Leu Asp Glu Ala Val
        595                 600                 605

Glu Arg Ser Leu Lys Ser Ile Leu Asn Lys Asn
610                 615
```

<210> SEQ ID NO 9
<211> LENGTH: 637

<212> TYPE: PRT
<213> ORGANISM: Mus musculus

<400> SEQUENCE: 9

```
Met Glu Gly Gly Cys Gly Ser Gln Trp Lys Ala Ala Gly Phe Leu Phe
1               5                   10                  15

Cys Val Met Val Phe Ala Ser Ala Glu Arg Pro Val Phe Thr Asn His
            20                  25                  30

Phe Leu Val Glu Leu His Lys Asp Gly Glu Glu Ala Arg Gln Val
        35                  40                  45

Ala Ala Glu His Gly Phe Gly Val Arg Lys Leu Pro Phe Ala Glu Gly
    50                  55                  60

Leu Tyr His Phe Tyr His Asn Gly Leu Ala Lys Ala Lys Arg Arg Arg
65                  70                  75                  80

Ser Leu His His Lys Arg Gln Leu Glu Arg Asp Pro Arg Ile Lys Met
                85                  90                  95

Ala Leu Gln Gln Glu Gly Phe Asp Arg Lys Lys Arg Gly Tyr Arg Asp
            100                 105                 110

Ile Asn Glu Ile Asp Ile Asn Met Asn Asp Pro Leu Phe Thr Lys Gln
        115                 120                 125

Trp Tyr Leu Phe Asn Thr Gly Gln Ala Asp Gly Thr Pro Gly Leu Asp
    130                 135                 140

Leu Asn Val Ala Glu Ala Trp Glu Leu Gly Tyr Thr Gly Lys Gly Val
145                 150                 155                 160

Thr Ile Gly Ile Met Asp Asp Gly Ile Asp Tyr Leu His Pro Asp Leu
                165                 170                 175

Ala Tyr Asn Tyr Asn Ala Asp Ala Ser Tyr Asp Phe Ser Ser Asn Asp
            180                 185                 190

Pro Tyr Pro Tyr Pro Arg Tyr Thr Asp Asp Trp Phe Asn Ser His Gly
        195                 200                 205

Thr Arg Cys Ala Gly Glu Val Ser Ala Ala Ser Asn Asn Ile Cys
    210                 215                 220

Gly Val Gly Val Ala Tyr Asn Ser Lys Val Ala Gly Ile Arg Met Leu
225                 230                 235                 240

Asp Gln Pro Phe Met Thr Asp Ile Ile Glu Ala Ser Ser Ile Ser His
                245                 250                 255

Met Pro Gln Leu Ile Asp Ile Tyr Ser Ala Ser Trp Gly Pro Thr Asp
            260                 265                 270

Asn Gly Lys Thr Val Asp Gly Pro Arg Glu Leu Thr Leu Gln Ala Met
        275                 280                 285

Ala Asp Gly Val Asn Lys Gly Arg Gly Gly Lys Gly Ser Ile Tyr Val
    290                 295                 300

Trp Ala Ser Gly Asp Gly Gly Ser Tyr Asp Asp Cys Asn Cys Asp Gly
305                 310                 315                 320

Tyr Ala Ser Ser Met Trp Thr Ile Ser Ile Asn Ser Ala Ile Asn Asp
                325                 330                 335

Gly Arg Thr Ala Leu Tyr Asp Glu Ser Cys Ser Ser Thr Leu Ala Ser
            340                 345                 350

Thr Phe Ser Asn Gly Arg Lys Arg Asn Pro Glu Ala Gly Val Ala Thr
        355                 360                 365

Thr Asp Leu Tyr Gly Asn Cys Thr Leu Arg His Ser Gly Thr Ser Ala
    370                 375                 380

Ala Ala Pro Glu Ala Ala Gly Val Phe Ala Leu Ala Leu Glu Ala Asn
385                 390                 395                 400
```

```
Leu Asp Leu Thr Trp Arg Asp Met Gln His Leu Thr Val Leu Thr Ser
            405                 410                 415

Lys Arg Asn Gln Leu His Asp Glu Val His Gln Trp Arg Arg Asn Gly
        420                 425                 430

Val Gly Leu Glu Phe Asn His Leu Phe Gly Tyr Gly Val Leu Asp Ala
        435                 440                 445

Gly Ala Met Val Lys Met Ala Lys Asp Trp Lys Thr Val Pro Glu Arg
450                 455                 460

Phe His Cys Val Gly Gly Ser Val Gln Asn Pro Glu Lys Ile Pro Pro
465                 470                 475                 480

Thr Gly Lys Leu Val Leu Thr Leu Lys Thr Asn Ala Cys Glu Gly Lys
                485                 490                 495

Glu Asn Phe Val Arg Tyr Leu Glu His Val Gln Ala Val Ile Thr Val
                500                 505                 510

Asn Ala Thr Arg Arg Gly Asp Leu Asn Ile Asn Met Thr Ser Pro Met
            515                 520                 525

Gly Thr Lys Ser Ile Leu Leu Ser Arg Arg Pro Arg Asp Asp Asp Ser
530                 535                 540

Lys Val Gly Phe Asp Lys Trp Pro Phe Met Thr Thr His Thr Trp Gly
545                 550                 555                 560

Glu Asp Ala Arg Gly Thr Trp Thr Leu Glu Leu Gly Phe Val Gly Ser
                565                 570                 575

Ala Pro Gln Lys Gly Leu Leu Lys Glu Trp Thr Leu Met Leu His Gly
                580                 585                 590

Thr Gln Ser Ala Pro Tyr Ile Asp Gln Val Val Arg Asp Tyr Gln Ser
            595                 600                 605

Lys Leu Ala Met Ser Lys Gln Glu Leu Glu Glu Leu Asp Glu
610                 615                 620

Ala Val Glu Arg Ser Leu Gln Ser Ile Leu Arg Lys Asn
625                 630                 635

<210> SEQ ID NO 10
<211> LENGTH: 299
<212> TYPE: PRT
<213> ORGANISM: Homo sapiens

<400> SEQUENCE: 10

Lys Val Glu Gln Ala Val Glu Thr Glu Pro Glu Pro Glu Leu Arg Gln
1               5                   10                  15

Gln Thr Glu Trp Gln Ser Gly Gln Arg Trp Glu Leu Ala Leu Gly Arg
            20                  25                  30

Phe Trp Asp Tyr Leu Arg Trp Val Gln Thr Leu Ser Glu Gln Val Gln
        35                  40                  45

Glu Glu Leu Leu Ser Ser Gln Val Thr Gln Glu Leu Arg Ala Leu Met
50                  55                  60

Asp Glu Thr Met Lys Glu Leu Lys Ala Tyr Lys Ser Glu Leu Glu Glu
65                  70                  75                  80

Gln Leu Thr Pro Val Ala Glu Glu Thr Arg Ala Arg Leu Ser Lys Glu
                85                  90                  95

Leu Gln Ala Ala Gln Ala Arg Leu Gly Ala Asp Met Glu Asp Val Arg
            100                 105                 110

Gly Arg Leu Val Gln Tyr Arg Gly Glu Val Gln Ala Met Leu Gly Gln
        115                 120                 125

Ser Thr Glu Glu Leu Arg Val Arg Leu Ala Ser His Leu Arg Lys Leu
```

```
                130              135              140
Arg Lys Arg Leu Leu Arg Asp Ala Asp Leu Gln Lys Arg Leu Ala
145                  150                  155                  160

Val Tyr Gln Ala Gly Ala Arg Glu Gly Ala Glu Arg Gly Leu Ser Ala
                 165                  170                  175

Ile Arg Glu Arg Leu Gly Pro Leu Val Glu Gln Gly Arg Val Arg Ala
                 180                  185                  190

Ala Thr Val Gly Ser Leu Ala Gly Gln Pro Leu Gln Glu Arg Ala Gln
                 195                  200                  205

Ala Trp Gly Glu Arg Leu Arg Ala Arg Met Glu Glu Met Gly Ser Arg
                 210                  215                  220

Thr Arg Asp Arg Leu Asp Glu Val Lys Glu Gln Val Ala Glu Val Arg
225                  230                  235                  240

Ala Lys Leu Glu Glu Gln Ala Gln Gln Ile Arg Leu Gln Ala Glu Ala
                 245                  250                  255

Phe Gln Ala Arg Leu Lys Ser Trp Phe Glu Pro Leu Val Glu Asp Met
                 260                  265                  270

Gln Arg Gln Trp Ala Gly Leu Val Glu Lys Val Gln Ala Ala Val Gly
                 275                  280                  285

Thr Ser Ala Ala Pro Val Pro Ser Asp Asn His
                 290                  295

<210> SEQ ID NO 11
<211> LENGTH: 317
<212> TYPE: PRT
<213> ORGANISM: Homo sapiens

<400> SEQUENCE: 11

Met Lys Val Leu Trp Ala Ala Leu Leu Val Thr Phe Leu Ala Gly Cys
1               5                   10                  15

Gln Ala Lys Val Glu Gln Ala Val Glu Thr Glu Pro Glu Pro Glu Leu
                 20                  25                  30

Arg Gln Gln Thr Glu Trp Gln Ser Gly Gln Arg Trp Glu Leu Ala Leu
                 35                  40                  45

Gly Arg Phe Trp Asp Tyr Leu Arg Trp Val Gln Thr Leu Ser Glu Gln
50                  55                  60

Val Gln Glu Glu Leu Leu Ser Ser Gln Val Thr Gln Glu Leu Arg Ala
65                  70                  75                  80

Leu Met Asp Glu Thr Met Lys Glu Leu Lys Ala Tyr Lys Ser Glu Leu
                 85                  90                  95

Glu Glu Gln Leu Thr Pro Val Ala Glu Glu Thr Arg Ala Arg Leu Ser
                 100                 105                 110

Lys Glu Leu Gln Ala Ala Gln Ala Arg Leu Gly Ala Asp Met Glu Asp
                 115                 120                 125

Val Arg Gly Arg Leu Val Gln Tyr Arg Gly Glu Val Gln Ala Met Leu
                 130                 135                 140

Gly Gln Ser Thr Glu Glu Leu Arg Val Arg Leu Ala Ser His Leu Arg
145                  150                 155                 160

Lys Leu Arg Lys Arg Leu Leu Arg Asp Ala Asp Asp Leu Gln Lys Arg
                 165                 170                 175

Leu Ala Val Tyr Gln Ala Gly Ala Arg Glu Gly Ala Glu Arg Gly Leu
                 180                 185                 190

Ser Ala Ile Arg Glu Arg Leu Gly Pro Leu Val Glu Gln Gly Arg Val
                 195                 200                 205
```

```
Arg Ala Ala Thr Val Gly Ser Leu Ala Gly Gln Pro Leu Gln Glu Arg
210                 215                 220

Ala Gln Ala Trp Gly Glu Arg Leu Arg Ala Arg Met Glu Glu Met Gly
225                 230                 235                 240

Ser Arg Thr Arg Asp Arg Leu Asp Glu Val Lys Glu Gln Val Ala Glu
                245                 250                 255

Val Arg Ala Lys Leu Glu Glu Gln Ala Gln Gln Ile Arg Leu Gln Ala
                260                 265                 270

Glu Ala Phe Gln Ala Arg Leu Lys Ser Trp Phe Glu Pro Leu Val Glu
                275                 280                 285

Asp Met Gln Arg Gln Trp Ala Gly Leu Val Glu Lys Val Gln Ala Ala
290                 295                 300

Val Gly Thr Ser Ala Ala Pro Val Pro Ser Asp Asn His
305                 310                 315

<210> SEQ ID NO 12
<211> LENGTH: 317
<212> TYPE: PRT
<213> ORGANISM: Homo sapiens

<400> SEQUENCE: 12

Met Lys Val Leu Trp Ala Ala Leu Leu Val Thr Phe Leu Ala Gly Cys
1               5                   10                  15

Gln Ala Lys Val Glu Gln Ala Val Glu Thr Glu Pro Glu Pro Glu Leu
                20                  25                  30

Arg Gln Gln Thr Glu Trp Gln Ser Gly Gln Arg Trp Glu Leu Ala Leu
            35                  40                  45

Gly Arg Phe Trp Asp Tyr Leu Arg Trp Val Gln Thr Leu Ser Glu Gln
50                  55                  60

Val Gln Glu Glu Leu Leu Ser Ser Gln Val Thr Gln Glu Leu Arg Ala
65                  70                  75                  80

Leu Met Asp Glu Thr Met Lys Glu Leu Lys Ala Tyr Lys Ser Glu Leu
                85                  90                  95

Glu Glu Gln Leu Thr Pro Val Ala Glu Glu Thr Arg Ala Arg Leu Ser
                100                 105                 110

Lys Glu Leu Gln Ala Ala Gln Ala Arg Leu Gly Ala Asp Met Glu Asp
            115                 120                 125

Val Cys Gly Arg Leu Val Gln Tyr Arg Gly Glu Val Gln Ala Met Leu
130                 135                 140

Gly Gln Ser Thr Glu Glu Leu Arg Val Arg Leu Ala Ser His Leu Arg
145                 150                 155                 160

Lys Leu Arg Lys Arg Leu Leu Arg Asp Ala Asp Asp Leu Gln Lys Arg
                165                 170                 175

Leu Ala Val Tyr Gln Ala Gly Ala Arg Glu Gly Ala Glu Arg Gly Leu
                180                 185                 190

Ser Ala Ile Arg Glu Arg Leu Gly Pro Leu Val Glu Gln Gly Arg Val
            195                 200                 205

Arg Ala Ala Thr Val Gly Ser Leu Ala Gly Gln Pro Leu Gln Glu Arg
210                 215                 220

Ala Gln Ala Trp Gly Glu Arg Leu Arg Ala Arg Met Glu Glu Met Gly
225                 230                 235                 240

Ser Arg Thr Arg Asp Arg Leu Asp Glu Val Lys Glu Gln Val Ala Glu
                245                 250                 255

Val Arg Ala Lys Leu Glu Glu Gln Ala Gln Gln Ile Arg Leu Gln Ala
                260                 265                 270
```

Glu Ala Phe Gln Ala Arg Leu Lys Ser Trp Phe Glu Pro Leu Val Glu
         275                 280                 285

Asp Met Gln Arg Gln Trp Ala Gly Leu Val Glu Lys Val Gln Ala Ala
290                 295                 300

Val Gly Thr Ser Ala Ala Pro Val Pro Ser Asp Asn His
305                 310                 315

<210> SEQ ID NO 13
<211> LENGTH: 299
<212> TYPE: PRT
<213> ORGANISM: Homo sapiens

<400> SEQUENCE: 13

Lys Val Glu Gln Ala Val Glu Thr Glu Pro Glu Pro Glu Leu Arg Gln
1               5                   10                  15

Gln Thr Glu Trp Gln Ser Gly Gln Arg Trp Glu Leu Ala Leu Gly Arg
            20                  25                  30

Phe Trp Asp Tyr Leu Arg Trp Val Gln Thr Leu Ser Glu Gln Val Gln
        35                  40                  45

Glu Glu Leu Leu Ser Ser Gln Val Thr Gln Glu Leu Arg Ala Leu Met
50                  55                  60

Asp Glu Thr Met Lys Glu Leu Lys Ala Tyr Lys Ser Glu Leu Glu Glu
65                  70                  75                  80

Gln Leu Thr Pro Val Ala Glu Glu Thr Arg Ala Arg Leu Ser Lys Glu
                85                  90                  95

Leu Gln Ala Ala Gln Ala Arg Leu Gly Ala Asp Met Glu Asp Val Cys
            100                 105                 110

Gly Arg Leu Val Gln Tyr Arg Gly Glu Val Gln Ala Met Leu Gly Gln
        115                 120                 125

Ser Thr Glu Glu Leu Arg Val Arg Leu Ala Ser His Leu Arg Lys Leu
130                 135                 140

Arg Lys Arg Leu Leu Arg Asp Ala Asp Asp Leu Gln Lys Arg Leu Ala
145                 150                 155                 160

Val Tyr Gln Ala Gly Ala Arg Glu Gly Ala Glu Arg Gly Leu Ser Ala
                165                 170                 175

Ile Arg Glu Arg Leu Gly Pro Leu Val Glu Gln Gly Arg Val Arg Ala
            180                 185                 190

Ala Thr Val Gly Ser Leu Ala Gly Gln Pro Leu Gln Glu Arg Ala Gln
        195                 200                 205

Ala Trp Gly Glu Arg Leu Arg Ala Arg Met Glu Glu Met Gly Ser Arg
210                 215                 220

Thr Arg Asp Arg Leu Asp Glu Val Lys Glu Gln Val Ala Glu Val Arg
225                 230                 235                 240

Ala Lys Leu Glu Glu Gln Ala Gln Gln Ile Arg Leu Gln Ala Glu Ala
                245                 250                 255

Phe Gln Ala Arg Leu Lys Ser Trp Phe Glu Pro Leu Val Glu Asp Met
            260                 265                 270

Gln Arg Gln Trp Ala Gly Leu Val Glu Lys Val Gln Ala Ala Val Gly
        275                 280                 285

Thr Ser Ala Ala Pro Val Pro Ser Asp Asn His
290                 295

<210> SEQ ID NO 14
<211> LENGTH: 4
<212> TYPE: PRT

```
-continued

<213> ORGANISM: Artificial Sequence
<220> FEATURE:
<223> OTHER INFORMATION: Synthetic sequence

<400> SEQUENCE: 14

Arg Leu Leu Arg
1

<210> SEQ ID NO 15
<211> LENGTH: 4
<212> TYPE: PRT
<213> ORGANISM: Artificial Sequence
<220> FEATURE:
<223> OTHER INFORMATION: Synthetic sequence

<400> SEQUENCE: 15

Leu Gln Lys Arg
1
```